United States Patent [19]
Saito

[11] Patent Number: 5,785,687
[45] Date of Patent: Jul. 28, 1998

[54] SYRINGE ASSEMBLY

[76] Inventor: Yoshikuni Saito, Ooaza Kitanogami 1930, Kurobanemachi, Nasu-gun, Tochigi-ken, Japan

[21] Appl. No.: 814,554

[22] Filed: Mar. 11, 1997

[30] Foreign Application Priority Data

Mar. 13, 1996 [JP] Japan .................. 8-084682

[51] Int. Cl.$^6$ ........................................ A61M 5/00
[52] U.S. Cl. ........................... 604/110; 604/195
[58] Field of Search ........................ 604/110, 187, 604/195, 198, 263

[56] References Cited

U.S. PATENT DOCUMENTS

| | | | |
|---|---|---|---|
| 4,888,002 | 12/1989 | Braginetz et al. | 604/195 |
| 5,122,124 | 6/1992 | Novacek et al. | 604/195 |
| 5,273,539 | 12/1993 | Chen | 604/110 |
| 5,531,705 | 7/1996 | Alter et al. | 604/110 X |
| 5,533,975 | 7/1996 | Lu | 604/110 |

*Primary Examiner*—John D. Yasko
*Attorney, Agent, or Firm*—Eckert Seamans Cherin & Mellott

[57] ABSTRACT

A projection for holding 10 is formed in an installation space 4b. A wall face 7a is formed in the installation space 4b on an arrow A side rather than the projection for holding 10. A main body 15a is provided so as to be linearly inserted in and pulled from the installation space 4b in a direction of an axial center P1. An abutting end face 16b is formed at the main body 15a so as to abut the abutting end face 16b on the wall face 7a in the direction as shown by the arrow A. A rib for holding 11 is annularly formed at the main body 15a along a plane perpendicular to the axis center P1. An engagement groove 25 is provided with the main body 15a so as to engage a piston 39. When the main body 15a is installed in the installation space 4b, the rib for holding 11 can be abutted on and engaged with the projection for holding 10 and the wall face 7a can be abutted on and engaged with the abutting end face 16b such that the main body 15a between the rib for holding 11 and the abutting end face 16b receives a predetermined compressive stress from the projection for holding 10 and the wall face 7a, and positions MQ1, MQ2 which are seal portions formed between the rib for holding 11 and the projection for holding 10 are formed with a width W3 smaller than any of a width W2 of the rib for holding and a width W1 of the projection for holding 10 in the direction as shown by the arrows A and B.

32 Claims, 15 Drawing Sheets

SYRINGE ASSEMBLY

BACKGROUND OF THE INVENTION

This invention relates to a syringe assembly, suitable for the use as a throwaway syringe assembly.

Since patient's blood included pathogenic bacteria adheres to a needle of a syringe assembly used, many throwaway syringe assemblies have been used for preventing secondary infection. As one of these throwaway syringe assemblies, various kinds of the syringe assemblies of needle retracting type, capable of discarding by inserting the needle having blood and the like after use into a syringe of the syringe assembly so as not to contact with the needle from the outside, have been proposed and used.

In the syringe assembly of the needle retracting type, generally, a predetermined needle holding member is attachably and detachably provided at the top end of the syringe body so as to connect the needle holding member with a needle. That is, when the needle is retracted into the syringe body, the needle holding member connected the needle therewith is retracted into the syringe body together with the needle. Therefore, the needle pulling-in type syringe assembly where the installation of the needle holding member on the syringe body is easily released with small force, then the pulling operation of the needle is easy, is desired. On the other hand, as the basic efficiency to be possesed by a syringe assembly, the needle holding member should be certainly fixed with respect to the syringe body and the portion between the syringe body and the needle holding member should be sealed when the needle holding member is installed on the syringe body.

As mentioned before, the desire to the needle pulling-in type syringe assembly is that the installation between the syringe body and the needle holding member is executed, certainly fixing the needle holding member with respect to the syringe body, extremely improving the sealing efficiency between the syringe body and the needle holding member, extremely easily releasing the installation of the needle holding member on the syringe body with small force.

An object of the present invention is to provide a syringe assembly where the installation between the syringe body and the needle holding member can be executed, certainly fixing the needle holding member with respect to the syringe body, extremely improving the sealing efficiency between the syringe body and the needle holding member, extremely easily releasing the installation of the needle holding member on the syringe body with small force, by applying to the needle pulling-in type syringe assembly, taking the above-mentioned circumstances into consideration.

SUMMARY OF THE INVENTION

Of the present invention, the 1st invention comprises a syringe assembly, comprising:
- a syringe body;
- a piston installed in said syringe body slidable in an axial center direction of said syringe body;
- a holding member installation space cylindrically formed at a top end of said syringe body;
- a penetrating hole formed at a top end of said holding member installation space communicating said holding member installation space and an outside of said syringe body with each other;
- a liquid flow thin tube holding member capable of connecting with a liquid flow thin tube member attachably and detachably connected with said holding member installation space, said syringe assembly further comprising:
- a projecting body for holding having a first width in said axial center direction of said syringe body, annularly formed along a plane perpendicular to said axial center direction of said syringe body at an inner peripheral portion of said holding member installation space;
- a stopper for holding formed in said holding member installation space on said top end side of said syringe body rather than said projecting body for holding;
- said liquid flow thin tube holding member having a member main body which can be linearly inserted in said holding member installation space in said axial center direction of said syringe body and can be linearly pulled out of said holding member installation space into said syringe body in said axial center direction of said syringe body;
- a stopper abutting portion formed at said member main body so as to abut the stopper abutting portion on said stopper for holding, facing said top end direction of said syringe body;
- a projection for holding having a second width in said axial center direction of said member main body, annularly formed along a plane perpendicular to said axial center direction of said member main body at an outer peripheral portion of said member main body;
- a member side engagement means provided with said member main body so as to be free to engage with said piston; and
- said syringe assembly wherein said projection for holding can be abutted on and engaged with said projecting body for holding and said stopper abutting portion can be abutted on and engaged with said stopper for holding respectively such that said member main body between said projection for holding and said stopper abutting portion receives a predetermined compressive stress from the projecting body for holding and said stopper for holding, and a seal portion formed between said projection for holding and said projecting body for holding is formed with a third width smaller than any of said second width of said projection for holding and said first width of said projecting body for holding in said axial center direction of said syringe body when said member main body is installed in said holding member installation space.

That is, the member main body is installed in the holding member installation space through the abutment and engagement between the projection for holding and the projecting body for holding and the abutment and engagement between the stopper abutting portion and the stopper for holding, thereby the liquid flow thin tube holding member is certainly fixed with respect to the syringe body. At the same time, the projection for holding and the projecting body for holding are abutted on each other with a predetermined contact pressure, that is, with a predetermined sealing pressure, thereby the portion between the projection for holding and the projecting body for holding is sealed by a seal portion, then the portion between the liquid flow thin tube holding member and the syringe body is certainly sealed. Especially, both of the projection for holding and the projecting body for holding projects, and the seal portion formed between the projection for holding and the projecting body for holding is formed with the THIRD width smaller than any of the second width of the projection for holding and the first width of the projecting body for holding in the axis center direction of the syringe body. Besides, the seal portion which is the abutting portion of both is annular line along the plane perpendicular to the axis center direction. Therefore, when the seal portion is seen by the section on the plane including the axis center, it shows point contact state or state close to point contact state. Then, high sealing efficiency can be exercised in comparison with the sealing by face contact. The installation and its release of the liquid flow thin tube holding member on and from the syringe body is executed by the abutment and its release between the projection for holding and the projecting body for holding. Besides, the abutment between the projection for holding and the projecting body for holding is executed in point contact state or the state close to the point contact state, as mentioned before. Therefore, when the liquid flow thin tube holding member is pulled off from the holding member installation space, the friction acting between these liquid flow thin tube holding member and the syringe body is small in comparison with the case where the engagement and installation of the liquid flow thin tube holding member with respect to the syringe body is executed by face contact. That is, the installation release of the liquid flow thin tube holding member from the syringe body can be extremely easily executed with small force. Furthermore, in the syringe assembly according to the present invention, the installation of the liquid flow thin tube holding member in the holding member installation space is executed by the abutment and engagement between the projection for holding and the projecting body for holding and between the stopper abutting portion and the stopper for holding, and the whole structure of the syringe assembly is extremely simple in comparison with a conventional syringe assembly, such as screwing type one. Then, when the liquid flow thin tube holding member is installed into the holding member installation space of the top end of the syringe body, there is no need to do anything but to linearly insert the liquid flow thin tube holding member into the holding member installation space in the axis center direction of the syringe body so as to engage the liquid flow thin tube holding member and the holding member installation space through the abutment by engagement between the projection for holding and the projecting body for holding and engagement between the stopper abutting portion and the stopper for holding. When the liquid flow thin tube holding member is taken off from the holding member installation space, it is necessary only to linearly operate the piston in the axis center direction of the syringe body so as to engage the liquid flow thin tube holding member and the piston with each other through the member side engagement means, and furthermore to linearly operate it in the axis center direction of the piston syringe body so as to pull the liquid flow thin tube holding member into the syringe body together with the piston, so it's simple. When the member main body is installed in the holding member installation space, the member main body between the projection for holding and the stopper abutting portion receives a predetermined compressive stress from the projecting body for holding and the stopper for holding. Then, as soon as the engagement between the projecting body for holding and the projection for holding is released, this compressive stress is released so as to spring the member main body out in the pulling in direction in the syringe body, thereby the liquid flow thin tube holding member can be smoothly pulled with further smaller force.

In the syringe assembly according to the 1st invention, the installation between the syringe body and the liquid flow thin tube holding member can be executed, certainly fixing the liquid flow thin tube holding member with respect to the syringe body, extremely improving the sealing efficiency between the sryinge body and the liquid flow thin tube holding member, extremely easily releasing the installation of the liquid flow thin tube holding member on the syringe body with small force. Besides, the whole structure of the syringe assembly can be made extremely simple, and then its assembly and operation can be made extremely easy.

In addition to the effects before-mentioned, at the time of the installation of the liquid flow thin tube holding member on the syringe body, the projecting body for holding annularly formed along the plane perpendicular to the axis center direction of the syringe body of the holding member installation space is immediately engaged with the projection for holding annularly formed along the plane perpendicular to the axis center direction of the liquid flow thin tube holding member linearly inserted in the holding member installation space in the axis center direction so as to position the liquid flow thin tube holding member at a predetermined position. Therefore, the positioning of the liquid flow thin tube holding member in the holding member installation space finishes only by inserting the liquid flow thin tube holding member without another specific operation, and at the same time, the sealing between the liquid flow thin tube holding member and the syringe body finishes, then extremely speedy assembly is possible.

Of the present invention, the 2nd invention comprises the syringe assembly of the 1st invention, wherein said projecting body for holding has a top end portion where a distance from said axial center of said syringe body is minimum, and a distance from said projecting body for holding to said axial center is made bigger for said top end direction of said syringe body on said top end side of said syringe body rather than said top end portion.

With this invention, the abutting and engagement position between the projecting body for holding and the projection for holding is on the top end side of the syringe body rather than the top end portion of the projecting body for holding. As explained before, the distance from the projecting body for holding to the axis center is made bigger for the top end direction of the syringe body on the top end side of the syringe body rather than the top end portion of the projecting body for holding. Therefore, the stress for the top end direction of the syringe body is added to the projection for holding abutting on the projecting body for holding whatever its shape is, so as to make the compressive stress compressing the member main body between the projecting body for holding and the stopper for holding. That is, in addition to the effects according to the 1st invention, the shape of the projection for holding can be freely planned than before, for this reason the production of the syringe assembly can be made easier.

Of the present invention, the 3rd invention comprises the syringe assembly of the 2nd invention, wherein a distance from said projecting body for holding to said axial center is made bigger for an rear end direction of said syringe body on said rear end side of said syringe body rather than said top end portion.

With this invention, in order to release the installation of the liquid flow thin tube holding member in the holding member installation space, the member main body is moved in the rear end direction of the syringe body with respect to the holding member installation space, then the projection for holding is moved in the rear end direction of the syringe body passing over the top end portion of the projecting body for holding. On this occasion, the abutment between the projecting body for holding and the projection for holding is executed such that the abutting position is on the rear end side of the syringe body rather than the top end portion of the projecting body for holding. Since the distance from the projecting body for holding to the axis center is made bigger for the rear end direction of the syringe body on the rear end side of the syringe body rather than the top end portion of the projecting body for holding as explained before, the stress for the rear end direction of the syringe body is added to the projection for holding abutting on the projecting body for holding whatever its shape is as the stress pressing the member main body in the rear end direction of the syringe body. That is, in addition to the effects of the 2nd invention, when the installation between the liquid flow thin tube holding member and the holding member installation space is released, the stress pressing the member main body in the rear end direction of the syringe body is acted from the projecting body for holding side to the member main body side, then the installation release can be executed with extremely small force, conveniently.

Of the present invention, the 4th invention comprises the syringe assembly of the 3rd invention, wherein a sectional shape by a plane including said axial center of said syringe body of said projecting body for holding is an arc shape.

With this invention, in addition to the effects of the 3rd invention, the seal portion which is the abutting portion of the projection for holding and the projecting body for holding is formed in point contact state or in the state close to the point contact state as long as the shape of the projection for holding is not an arc shape matching and corresponding with the projecting body for holding. Therefore, further high sealing efficiency can be exercised. Besides, there will be few breaks, conveniently, because of its arc shape.

Of the present invention, the 5th invention comprises the syringe assembly of the 3rd invention, wherein a sectional shape by a plane including said axial center of said syringe body of said projecting body for holding is an triangle shape.

With this invention, in addition to the effects of the 3rd invention, forming of the projecting body for holding is easy since the shape is simple in comparison with the arc shape or the like.

Of the present invention, the 6th invention comprises the syringe assembly of the 1st invention, wherein a sectional shape by a plane including said axial center of said syringe body of said projecting body for holding is a square shape.

With this invention, in addition to the effects of the 1st invention, forming of the projecting body for holding is easy since the shape is simple in comparison with the arc shape or the like.

Of the present invention, the 7th invention comprises the syringe assembly of the 1st invention, wherein said projection for holding has a projection top end portion where a distance from said axial center of said member main body is maximum, and a distance from said projection for holding to said axial center is made smaller for said rear end direction of said member main body on said rear end side of said member main body rather than said projection top end portion.

With this invention, the abutting and engagement position between the projecting body for holding and the projection for holding is on the rear end side of the member body rather than the projection top end portion of the projection for holding. As explained before, the distance from the projection for holding to the axis center is made smaller for the rear end direction of the member main body on the rear end side of the member main body rather than the projection top end portion of the projection for holding. Therefore, the stress for the rear end direction of the syringe body is added to the projecting body for holding abutting on the projection for holding whatever its shape is, then, the stress for the top end direction of the member main body, that is, the compressive stress compressing the member main body between the projecting body for holding and the stopper for holding is added to the projection for holding as its reaction. That is, in addition to the effects according to the 1st invention, the shape of the projecting body for holding can be freely planned than before, for this reason the production of the syringe assembly can be made easier.

Of the present invention, the 8th invention comprises the syringe assembly of the 7th invention, wherein said distance from said projection for holding to said axial center is made smaller for said top end direction of said member main body on said top end side of said member main body rather than said projection top end portion.

With this invention, in order to release the installation of the liquid flow thin tube holding member in the holding member installation space, the member main body is moved in the rear end direction of the syringe body with respect to the holding member installation space, then the projecting body for holding is relatively moved in the top end direction of the syringe body passing over the projection top end portion of the projection for holding. On this occasion, the abutment between the projecting body for holding and the projection for holding is executed such that the abutting position is on the top end side of the member body rather than the projection top end portion of the projection for holding. Since the distance from the projection for holding to the axis center is made smaller for the top end direction of the member main body on the top end side of the member main body rather than the projection top end portion of the projection for holding as explained before, the stress for the top end direction of the syringe body is added to the projecting body for holding abutting on the projection for holding whatever its shape is, then the stress for the rear end direction of the member main body, that is, the stress pressing the member main body in the rear end direction of the syringe body is added to the projection for holding as its reaction. That is, in addition to the effects of the 7th invention, when the installation between the liquid flow thin tube holding member and the holding member installation space is released, the stress pressing the member main body in the rear end direction of the syringe body is acted from the projecting body for holding side to the member main body side, then the installation release can be executed with extremely small force, conveniently.

Of the present invention, the 9th invention comprises the syringe assembly of the 8th invention, wherein a sectional shape by a plane including said axial center of said member main body of said projection for holding is an arc shape.

With this invention, in addition to the effects of the 8th invention, the seal portion which is the abutting portion of the projection for holding and the projecting body for holding is formed in point contact state or in the state close to the point contact state as long as the shape of the projecting body for holding is not an arc shape matching and corresponding with the projection for holding. Therefore, further high sealing efficiency can be exercised. Besides, there will be few breaks, conveniently, because of its arc shape.

Of the present invention, the 10th invention comprises the syringe assembly of the 8th invention, wherein a sectional shape by a plane including said axial center of said member main body of said projection for holding is a triangle shape.

With this invention, forming of the projection for holding is easy.

Of the present invention, the 11th invention comprises the syringe assembly of the 1st invention, wherein a sectional shape by a plane including said axial center of said member main body of said projection for holding is a square shape.

With this invention, in addition to the effects of the 1st invention, forming of the projecting body for holding is easy since the shape is simple in comparison with the arc shape or the like.

Of the present invention, the 12th invention comprises the syringe assembly of the 1st invention, wherein said projecting body for holding has a top end portion where a distance from said axial center of said syringe body is minimum, said projection for holding has a projection top end portion where a distance from said axial center of said member main body is maximum, and a seal portion which said projection for holding and said projecting body for holding abut on each other when said member main body is installed in said holding member installation space is between said top end portion and said projection top end portion in said axial center direction of said syringe body.

With this invention, in the state that the member main body is installed in the holding member installation space, even if the projection for holding were about to move with respect to the projecting body for holding in the rear end direction of the syringe body, so the projecting body for holding were about to move in the top end direction of the member main body to the projection for holding, because the portion near the top end portion of the projecting body for holding and the portion near the projection top end portion of the projection for holding exist such that one prevents the other's movement, in the state the member main body is installed in the holding member installation space, inadvertently moving the projection for holding to the projecting body for holding, that is, inadvertently moving the projecting body for holding to the projection for holding would be extremely saved. Therefore, in addition to the effects of the 1st invention, inadvertently taking off the member main body installed in the holding member installation space is saved, and its safety is high.

Of the present invention, the 13th invention comprises the syringe assembly of the 1st invention, wherein an outside diameter of portions excluding said projection for holding of said member main body is formed smaller than an inside diameter of a portion corresponding to said holding member installation space.

With this invention, the liquid flow thin tube holding member and the holding member installation space can contact with each other only through the projection for holding. In addition to the effects of the 1st invention, the attachment and detachment of the liquid flow thin tube holding member to and from the holding member installation space is further easy. And, it is possible to easily and smoothly set the liquid flow thin tube holding member at the time of an assembly and to easily and smoothly pull the needle after use in the syringe assembly of the liquid flow thin tube member.

Of the present invention, the 14th invention comprises the syringe assembly of the 1st invention, wherein said liquid flow thin tube holding member can be inserted into said holding member installation space through said penetrating hole.

With this invention, in addition to the effects of the 1st invention, the installation of the liquid flow thin tube holding member in the holding member installation space can be executed in the state the piston is installed in the syringe body. Then, the possibility of entering dust into the syringe body at the time of the installation can be decreased, so it's hygienic.

Of the present invention, the 15th invention comprises the syringe assembly of the 14th invention, wherein one or more than one slits are formed at a periphery of said penetrating hole.

With this invention, in addition to the effects of the 14th invention, the liquid flow thin tube holding member can be easily inserted and installed in the holding member installation space through the penetrating hole side by making use of elastic deformation of the slits.

Of the present invention, the 16th invention comprises the syringe assembly of the 1st invention, wherein a needle main body is directly connected with said member main body.

With this invention, in addition to the effects of the 1st invention, the member main body becomes to be so-called hub for connecting the needle, then the number of parts of the whole syringe assembly is extremely small. Therefore, the syringe assembly which whole structure is extremely simple is provided and its assembly is further made simple.

Of the present invention, the 17th invention comprises the syringe assembly of the 16th invention, wherein said member side engagement means and said needle main body are communicated with each other.

With this invention, when the top end portion of the piston and the liquid flow thin tube holding member are engaged with each other through the member side engagement means by pressing the piston, a liquid, such as the injection liquid remaining near the member side engagement means is to be compressed between the top end portion of the piston and the liquid flow thin tube holding member. But, the liquid to be compressed appropriately flows to the needle main body side communicating with the member side engagement means so as to escape. That is, in addition to the effects of the 16th invention, compressing the liquid between the top end portion of the piston and the liquid flow thin tube holding member is extremely saved, so the engagement between the top end portion of the piston and the liquid flow thin tube holding member can be executed with extremely small force, conveniently.

Of the present invention, the 18th invention comprises the syringe assembly of the 1st invention, wherein a taper for connecting liquid flow thin tube member is formed on said top end side of said member main body, projecting in a direction parallel to said axial center direction of said member main body.

With this invention, in the syringe assembly according to the 18th invention, the liquid flow thin tube member comprised of the member in the shape of a cone (so-called hub) for connecting the needle main body or the member, such as the tube for blood transfusion and the tube for intravenous drip with the member can be installed on the taper for connecting liquid flow thin tube member. That is, the present invention is used for the LUER-LOCK type or LUER-FIT type syringe assembly. That is, it is possible to attach and detach the liquid flow thin tube member to and from the taper for connecting liquid flow thin tube member. Then, the change of the liquid flow thin tube member with respect to the syringe assembly can be easily executed by the attachment and detachment between the taper for connecting liquid flow thin tube member and the hub at the site while the liquid flow thin tube holding member is being installed in the holding member installation space. Then, in addition to the effects of the 1st invention, the assembly and operation of the syringe assembly is further made easy.

Of the present invention, the 19th invention comprises the syringe assembly of the 18th invention, wherein a liquid flow thin tube member engagement portion is provided at a periphery of said taper for connecting liquid flow thin tube member of said member main body.

That is, the present invention is used for a LUER-LOCK type syringe assembly. Then, in addition to the effects of the 18th invention, when the liquid flow thin tube member is installed on the taper for connecting liquid flow thin tube member, it is engaged with the liquid flow thin tube member engagement portion, then the installation of the liquid flow thin tube member on the liquid flow thin tube holding member is certain, conveniently.

Of the present invention, the 20th invention comprises the syringe assembly of the 19th invention, wherein said liquid flow thin tube member engagement portion is a screw hole for installation cylindrically formed opening in a direction parallel to said axial center direction of said member main body.

With this invention, in addition to the effects of the 19th invention, the installation of the liquid flow thin tube member on the liquid flow thin tube holding memer is further certain by the fitting and engagement between the liquid flow thin tube member and the screw hole for installation, conveniently.

Of the present invention, the 21st invention comprises the syringe assembly of the 15th invention, wherein said taper for connecting liquid flow thin tube member is formed on said top end side of said member main body, projecting in a direction parallel to said axial center direction of said member main body.

With this invention, in the syringe assembly according to the 21st invention, it is possible to attach and detach the liquid flow thin tube member to and from the taper for connecting liquid flow thin tube member. Then, the change of the liquid flow thin tube member with respect to the syringe assembly can be easily executed by the attachment and detachment between the taper for connecting liquid flow thin tube member and the liquid flow thin tube member at the site while the liquid flow thin tube holding member is being installed in the holding member installation space. Then, in addition to the effects of the 15th invention, the assembly and operation of the syringe assembly is further made easy.

Of the present invention, the 22nd invention comprises the syringe assembly of the 18th invention, wherein a rotation stop portion is formed at an inner peripheral portion of said holding member installation space, and a peripheral direction abutting portion is formed at an outer periphery portion of said member main body so as to prevent rotation of said member main body in a periphery direction with said axial center of said syringe body as its center by abutment in said periphery direction between said peripheral direction abutting portion and said rotation stop portion when said member main body is installed in said holding member installation space.

With this invention, in the syringe assembly according to the 22nd invention, when a predetermined liquid flow thin tube member is installed on the liquid flow thin tube holding member installed on the syringe body through the taper for connecting liquid flow thin tube member, the member main body of the liquid flow thin tube holding member is prevented from moving in the peripheral direction of the member main body together with the liquid flow thin tube member by abutting the peripheral direction abutting portion on the rotation stop portion in the peripheral direction even if it would be rotated with respect to the syringe body in the peripheral direction. That is, in addition to the effects of the 18th invention, the installation of the liquid flow thin tube member on the liquid flow thin tube holding member is made easy.

Of the present invention, the 23rd invention comprises the syringe assembly of the 19th invention, wherein a rotation stop portion is formed at an inner peripheral portion of said holding member installation space, and a peripheral direction abutting portion is formed at an outer periphery portion of said member main body so as to prevent rotation of said member main body in a periphery direction with said axial center of said syringe body as its center by abutment in said periphery direction between said peripheral direction abutting portion and said rotation stop portion when said member main body is installed in said holding member installation space.

With this invention, in the syringe assembly according to the 23rd invention, when a predetermined liquid flow thin tube member is installed on the liquid flow thin tube holding member installed on the syringe body through the taper for connecting liquid flow thin tube member, the member main body of the liquid flow thin tube holding member is to be moved in the peripheral direction with respect to the syringe body together with the liquid flow thin tube member. But, by abutting the peripheral direction abutting portion on the rotation stop portion in the peripheral direction, the rotation of the member main body in the peripheral direction is prevented. That is, the installation of the liquid flow thin tube member on the liquid flow thin tube holding member is made easy.

Of the present invention, the 24th invention comprises the syringe assembly of the 1st invention, wherein said member side engagement means has a groove formed in a direction perpendicular to said axial center direction of said member main body, penetrating said member main body.

With this invention, in addition to the effects of the 1st invention, machining and forming of the member side engagement means on the member main body is executed only by penetrating the member main body so as to form a groove, so it's easy. Besides, when the top end portion of the piston and the member main body are engaged with each other through the member side engagement means by pressing the piston, a liquid, such as the injection liquid remaining in the member side engagement means, is to be compressed between the top end portion of the piston and the member main body. But, since the member side engagement means has the groove formed penetrating the member main body in the direction perpendicular to the axis center direction of the member main body, the liquid appropriately flows through the groove in the direction perpendicular to the axis center direction of the member main body, in the direction away from the axis center so as to escape to the side of the member main body. That is, the liquid remaining in the member side engagement means is extremely prevented from being compressed between the top end portion of the piston and the member main body, then the engagement between the top end portion of the piston and the member main body is executed with extremely small force, conveniently.

Of the present invention, the 25th invention comprises the syringe assembly of the 1st invention, wherein a deformation accelerating groove is provided with said member main body on a side in a direction perpendicular to said axial center direction of said member main body of said member side engagement means.

With this invention, the deformation near the holding member side engagement means of the member main body is extremely easy because of the deformation accelerating groove. Then, in addition to the effects of the 1st invention, the engagement between the top end portion of the piston and the member main body through the member side engagement means by deforming the member side engagement means can be easily executed with extremely small force.

Of the present invention, the 26th invention comprises the syringe assembly of the 1st invention, wherein a piston side engagement means capable of engaging with said member side engagement means of said liquid flow thin tube holding member is provided with said piston, facing said member side engagement means.

With this invention, in addition to the effects of the 1st invention, the liquid flow thin tube holding member after use can be engaged with the piston side engagement means of the piston so as to be pulled off in the syringe body together with the liquid flow thin tube member, such as a needle. The needle after use can be easily pulled in the syringe body only by pressing and pulling operation of the piston, the same operation as an usual syringe assembly. Then, its operation is easy for everyone, there is no danger of error operation, and safety is high.

Of the present invention, the 27th invention comprises the syringe assembly of the 1st invention, wherein said piston is comprised such that a piston body can be bent and taken off between an operation portion and a medical liquid pressing portion.

With this invention, in addition to the effects of the 1st invention, the liquid flow thin tube member, such as the needle, can be left holded at the top end portion of the piston, held in the syringe body, in the syringe body, in inoperable state from outside by bending and taking the piston. The safety at the time of disposal work thereafter is high.

Of the present invention, the 28th invention comprises the syringe assembly of the 27th invention, wherein a piston stopper is provided with said syringe body so as not to pull off said medical liquid pressing portion of said piston from said syringe body.

With this invention, in addition to the effects of the 27th invention, hurting an operator with the needle after use by inadvertently pulling the piston off from the syringe body is saved when the piston is moved together with the needle, then, safety is high.

Of the present invention, the 29th invention comprises the syringe assembly of the 27th invention, wherein a notch for bending and taking off is formed at said piston body of said piston.

With this invention, the operation of bending and taking the piston can be executed by making use of the notch.

Of the present invention, the 30th invention comprises the syringe assembly of the 29th invention, wherein said notch is formed so as to position at an end portion of said syringe body when said piston is abutted on said piston stopper.

With this invention, the piston is pulled till the abutment on the piston stopper, and then, the piston can be immediately bent and taken off by making use of the end portion, the storage and remaining operation of the needle in the syringe body can be successively executed, and effective injection and disposal operation is possible.

Of the present invention, the 31st invention comprises the syringe assembly of the 1st invention, wherein said member main body is formed with a material softer than one forming said projecting body for holding of said syringe body.

With this invention, when the projection for holding of the member main body and the projecting body for holding of the syringe body are abutted and engaged with each other, the projection for holding appropriately elastically deforms because of its flexibility so as to be easy to closely contact with the projecting body for holding. At the result, the sealing between the projection for holding and the projecting body for holding is more certain, and the fixing of the member main body with respect to the syringe body is made more certain.

Of the present invention, the 32nd invention comprises the syringe assembly of the 1st invention, wherein said member main body is formed by a method of forming with two different materials, having a first material and a second material softer than the first material and softer than the material forming said projecting body for holding of said syringe body, and said projection for holding is formed with the second material.

With this invention, when the projection for holding is abutted on and engaged with the projecting body for holding of the syringe body side, the projection for holding elastically deforms because of its flexibility so as to be easy to closely contact with the projecting body for holding. At the result, the sealing between the projection for holding and the projecting body for holding is more certain, and the fixing of the liquid flow thin tube holding member with respect to the syringe body is made more certain.

DESCRIPTION OF THE PREFERRED EMBODIMENT

Embodiments of the present invention will now be described hereinafter with respect to the accompanying drawings.

Figure 1:
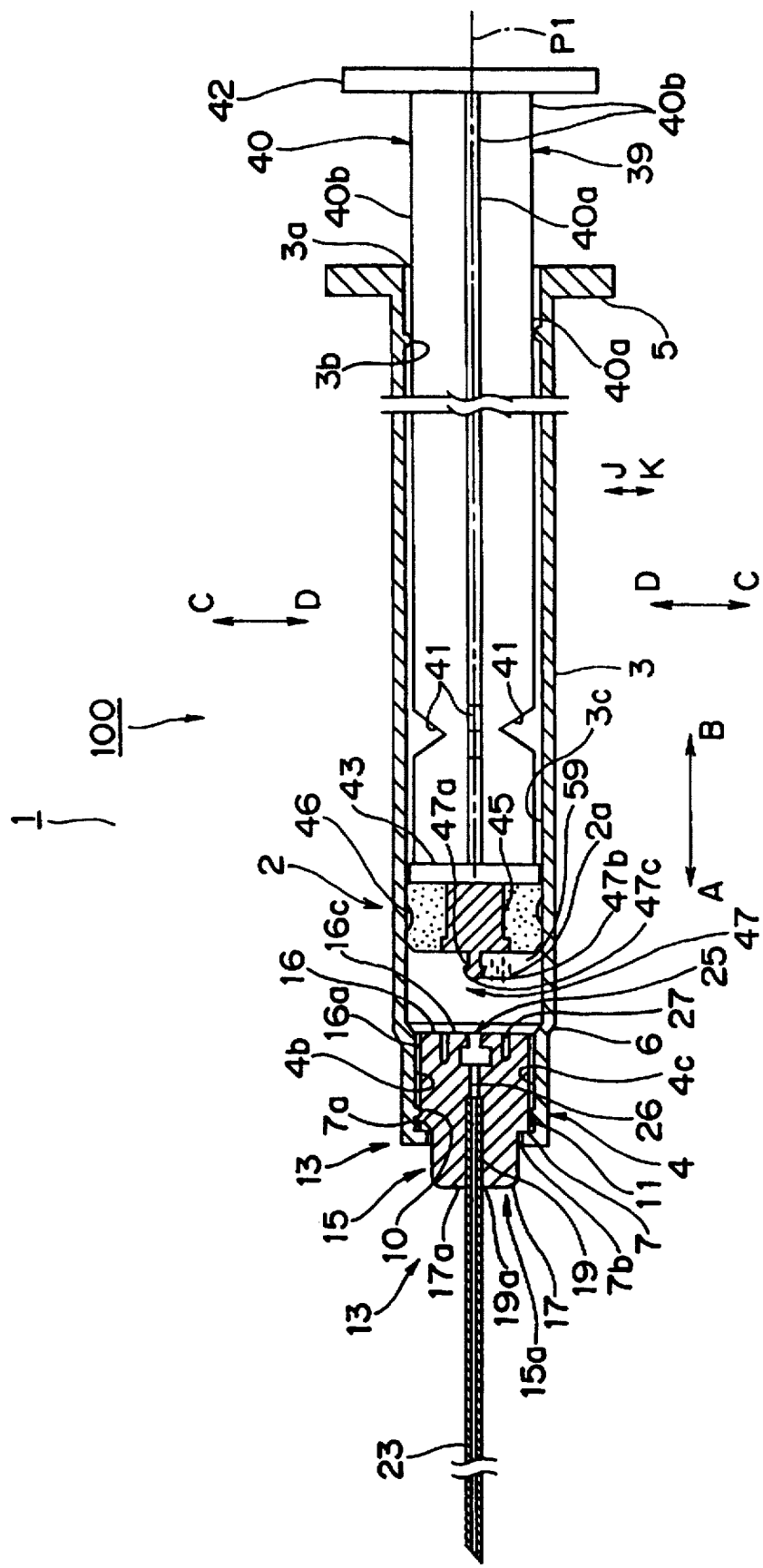
FIG. 1 is a typical sectional view showing an example of a syringe assembly according to the present invention.

A syringe assembly 1 has a syringe 100 made of resin, as shown in FIG. 1. A syringe body 2 is provided with the syringe 100 (FIG. I is a typical sectional view of the syringe assembly 1, but a side is shown in a part of a piston 39, described hereinafter, not the section, for convenience.). A main cylindrical portion 3, cylindrically formed, is provided with the syringe body 2. A direction of an axis center of the main cylindrical portion 3, that is, the reciprocating directions parallel to an axis center P1 are an arrow A direction in the figure (or the left direction of the paper of FIG. 1.) and an arrow B direction (or the right direction of the paper of FIG. 1). That is, the direction as shown by the arrows A and B is one of the axis center of the syringe body 2.

On the outer periphery side of the main cylindrical portion 3, a syringe support 5, being in the shape of a plate, is provided near an opening end 3a of the arrow B side of the main cylindrical portion 3 in such a manner as forming a flange of the main cylindrical portion 3. On an inner peripheral face 3c side of the main cylindrical portion 3, an engagement rib 3b, projecting in the direction for the axis center P1 of the main cylindrical portion 3, that is, the direction as shown by an arrow D of the figure, is annularly formed near the opening end 3a along the inner peripheral face 3c.

Figure 2:
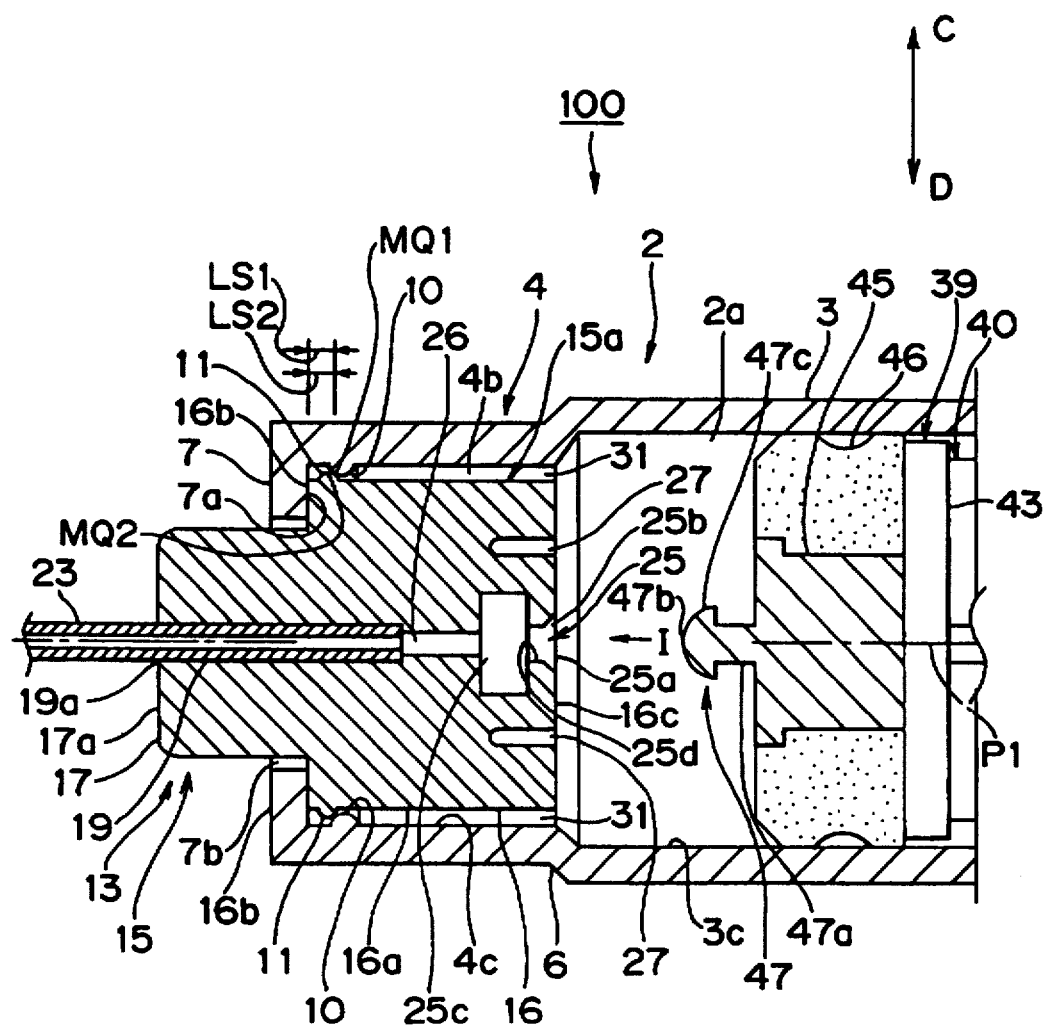
FIG. 2 is an enlarged sectional view in a portion near an installation space of the syringe assembly as shown in FIG. 1.

On the arrow A side of the main cylindrical portion 3, a taper 6 in the shape of a funnel is formed unitedly connecting with the main cylindrical portion 3, as shown in FIGS. 1 and 2. The inside diameter in the section perpendicular to the direction as shown by the arrows A and B of the taper 6 (that is, the circular section) is made narrower for the direction as shown by the arrow A. The inside of the main cylindrical portion 3 and the inside of the taper 6 communicate with each other in the direction as shown by the arrows A and B, and the space which consists of both insides combined is an inside space 2a of the syringe body 2.

Figure 3:
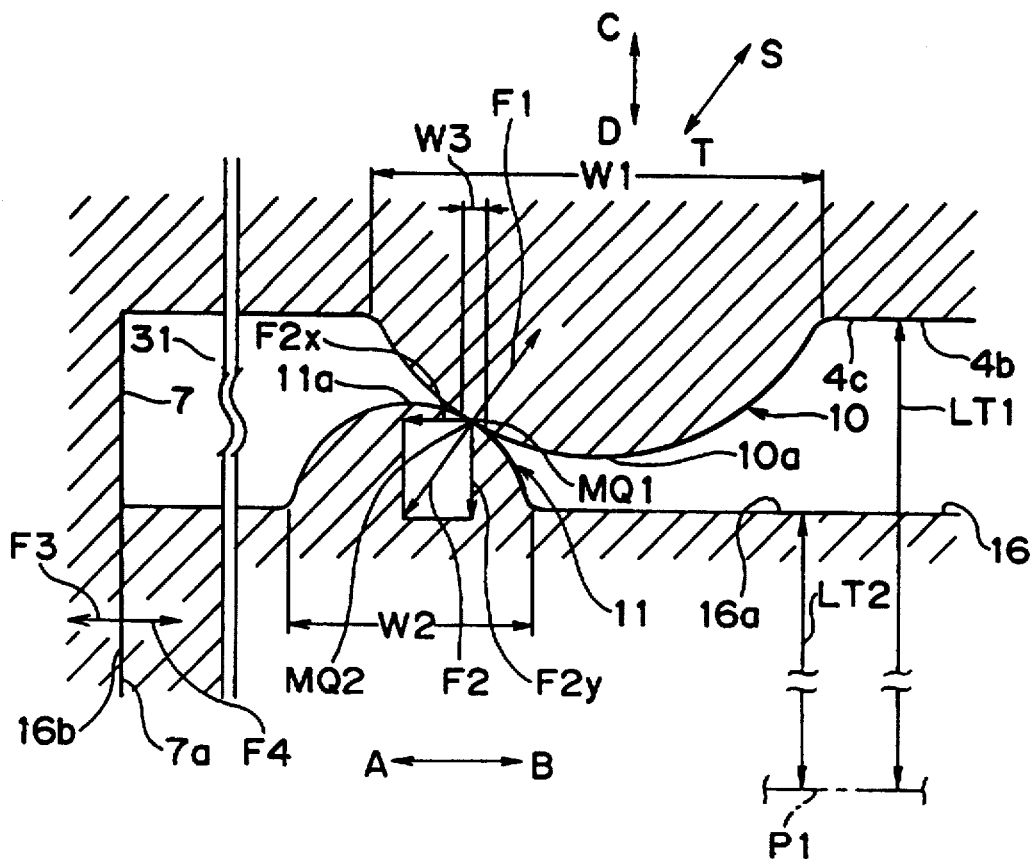
FIG. 3 is an enlarged sectional view showing a projection for holding and a rib for holding as shown in FIG. 2.
Figure 5:
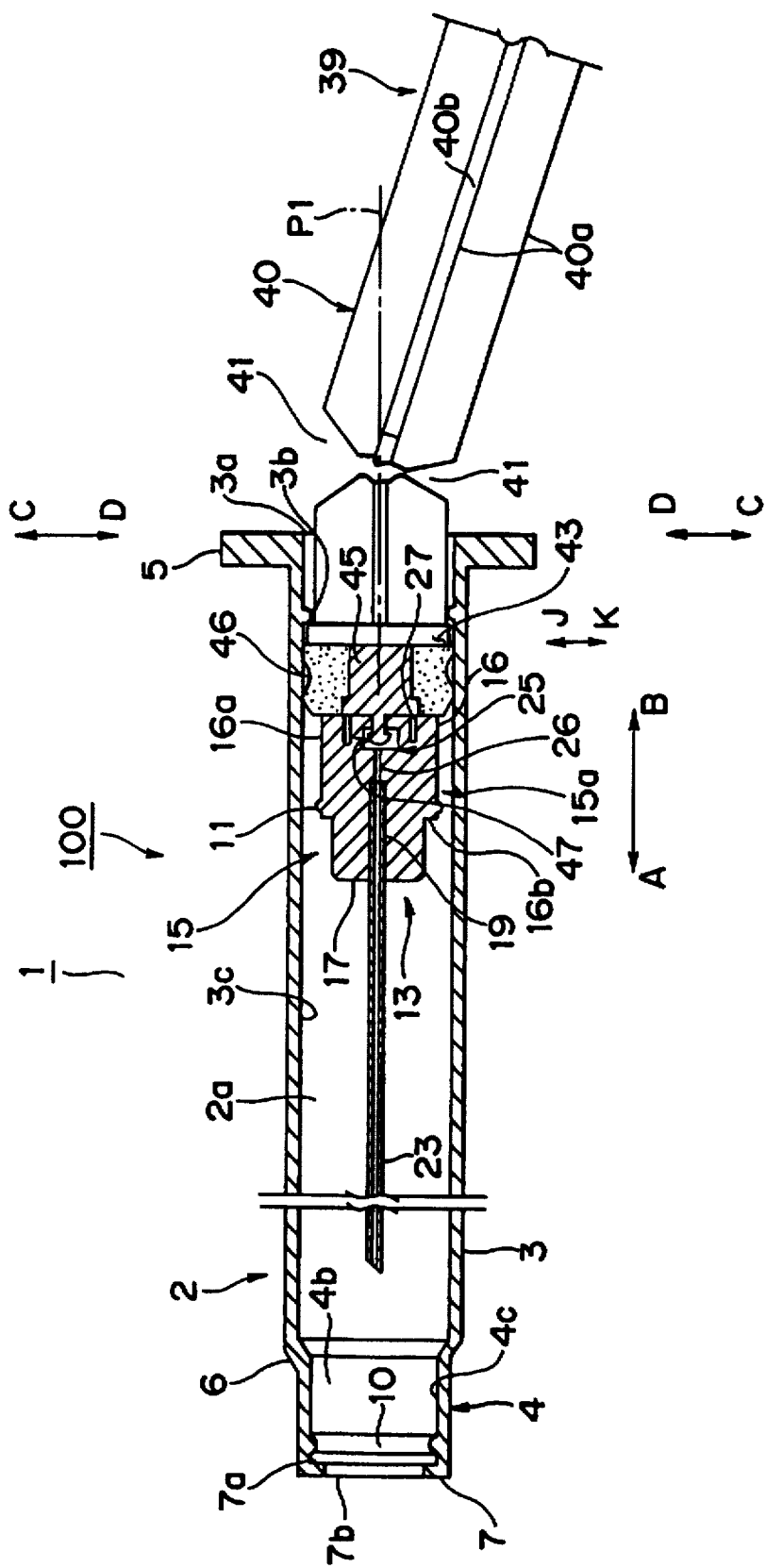
FIG. 5 is a view showing a piston is bent and taken off in the syringe assembly as shown in FIG. 1.

On the side of the arrow A of the taper 6, that is, on the side of the top of the syringe body 2, as shown in FIGS. 1, 2 and 5, a cylindrical installation portion 4, which center is basically the axis center P1, is formed unitedly connecting with the taper 6 extending in the direction as shown by the arrow A. Then, the installation portion 4 has an installation space 4b in the shape of a cylinder therein. At the top end portion of the arrow A side of the installation space 4b, an end wall portion 7 projecting in the direction as shown by the arrow D of the figure is formed along a plane perpendicular to the axis center P1. A penetrating hole 7b open in an almost circular shape with the axis center P1 as its center is provided with the end wall portion 7 communicating the installation space 4b and the outside of the syringe body 2 with each other in the direction as shown by the arrows A and B. Furthermore, near the penetrating hole 7b of the inner peripheral portion of the installation space 4b, that is, at the position of the arrow B side of the penetrating hole 7b, a projection for holding 10 is formed. That is, the projection for holding 10 is formed in the shape of a rib projecting in the direction as shown by the arrow D of the figure from the inner peripheral portion of the installation space 4b and the projection for holding 10 is annularly formed basically forming a stripe along the inner peripheral portion of the installation space 4b, and along the plane perpendicular to the direction as shown by the arrows A and B. The section of the projection for holding 10 on the plane including the axis center P1 is an arc shape as shown in FIG. 3. That is, the projection for holding 10 has a top end 10 where a distance LT1 from the axis center P1 is minimum. The distance LT1 is made bigger for the direction as shown by the arrow A from the top end10a and is made bigger for the direction as shown by the arrow B from the top end10a.

The syringe 100 before-mentioned is comprised of the syringe body 2 and the syringe support 5 unitedly forming. The syringe body 2 is comprised of the main cylindrical portion 3, the taper 6, the installation portion 4 unitedly forming.

On the other hand, a needle installation unit 13 is installed in the installation space 4b, as shown in FIGS. 1 and 2. The needle installation unit 13 has a needle installation body 15 attachably and detachably inserted in the installation space 4b. In this embodiment, the needle installation body 15 is a hub for connecting a needle. That is, the needle installation body 15 has a main body 15a basically forming a cylinder, which is linearly inserted in the installation space 4b from the rear end side of the syringe body 2, that is, from the opening end 3a side of the syringe body 2 via the inside space 2a in the direction as shown by the arrow A and is linearly pulled from the installation space 4b in the inside space 2a of the syringe body 2 in the direction as shown by the arrow B. Furthermore, the main body 15a has a pillar portion 16 in the shape of a cylinder. On an outside peripheral face 16a side of the pillar portion 16, a rib for holding 11 is formed projecting in the direction as shown by an arrow C. The rib for holding 11 is an annular stripe along the plane perpendicular to the direction of the axis center of the pillar portion 16, then, of the axis center of the main body 15a (which corresponds with the axis center P1 in the case of the present embodiment), that is, in the direction as shown by the arrows A and B of the figure, and is formed along the outside peripheral face 16a. The section of the projection for holding 10 on the plane including axis center P1 is an arc as shown in FIG. 3. That is, the rib for holding 11 has a top end 11a where a distance LT2 from the axis center P1 is maximum. The distance LT2 is made smaller for the direction as shown by the arrow A on the arrow A side from the top end 11a, and the distance LT2 is made smaller for the direction as shown by the arrow B on the arrow B side from the top end 11a.

The outside diameter of the portion excluding the rib for holding 11 of the pillar portion 16 is smaller than the inside diameter of the installation space 4b, the inside diameter of the portion excluding the projection for holding 10 of the installation space 4b is bigger than the outside diameter of the pillar portion 16. Accordingly, a spacing 31 is formed between the outside peripheral face 16a of the pillar portion 16 and an inner peripheral face 4c of the installation space 4b. The outside diameter at the position of the rib for holding 11 of the pillar portion 16 is smaller than the inside diameter of the portion excluding the projection for holding 10 of the installation space 4b, and the inside diameter at the position of the projection for holding 10 of the installation space 4b is bigger than the outside diameter of the portion excluding the rib for holding 11 of the pillar portion 16. In the state that the needle installation body 15 is installed in the installation space 4b, the top end 11a of the rib for holding 11 does not reach the level of the inner peripheral face 4c of the installation space 4b and the top end 10a of the projection for holding 10 does not reach the level of the outside peripheral face 16a of the pillar portion 16.

On the arrow A side of the pillar portion 16, a small pillar portion 17, which diameter is smaller than one of the pillar portion 16, being concentric with the pillar portion 16, is provided being united with the pillar portion 16. The diameter of the small pillar portion 17 is rather smaller than one of the penetrating hole 7b. The diameter of the pillar portion 16 is bigger than one of the penetrating hole 7b, then an abutting end face 16b facing the direction as shown by the arrow A is formed by the difference of the diameter of the pillar portion 16 and the diameter of the small pillar portion 17 at the end portion of the arrow A side of the pillar portion 16 for the direction as shown by the arrow A, that is, for the top end direction of the syringe body 2 (that is, the direction facing the penetrating hole 7b). In the state that the needle installation body 15 is inserted and installed in the installation space 4b, the abutting end face 16b of the pillar portion 16 abuts on a wall face 7a of the arrow B side of the end wall portion 7.

Besides, in this state, the rib for holding 11 abuts on the projection for holding 10 of the installation space 4b with a predetermined contact pressure. As shown in FIG. 3, this abutment realizes in such a manner that a position MQ1 of the arrow B side rather than the top end 11a of the rib for holding 11 in the rib for holding 11 and a position MQ2 of the arrow A side rather than the top end portion 10a of the projection for holding 10 in the projection for holding 10 contact with each other. That is, the positions MQ1, MQ2 are seal portions which are abutting positions between the rib for holding 11 and the projection for holding 10, and are between the top end 10a and the top end 11a in the direction as shown by the arrows A and B. Then, a contact pressure F1 in the direction as shown by an arrow S (the direction comprised of the positive component of the direction as shown by the arrow B and the positive component of the direction as shown by the arrow C of the figure) acts on the projection for holding 10 from the rib for holding 11, as shown in FIG. 3. A contact pressure F2 as the reaction of the contact pressure F1 acts on the rib for holding 11 from the projection for holding 10 in the direction as shown by an arrow T opposite to the direction as shown by the arrow S. As shown in FIG. 3, a contact pressure F3 in the direction as shown by the arrow A acts on the end wall portion 7 from the pillar portion 16 between the abutting end face 16b of the pillar portion 16 and the wall face 7a of the arrow B side of the end wall portion 7. A contact pressure F4 as the reaction of the contact pressure F3 acts on the pillar portion 16 from the end wall portion 7 in the direction as shown by the arrow B.

If the component force of the contact pressure F2 in the direction as shown by the arrows A and B is a component force F2x and the component force in the direction as shown by the arrows C and D is a component force F2y, the degree of the contact pressure F4 is equal to the degree of the component force F2x, and both are matched with each other compressing the pillar portion 16 in the direction as shown by the arrows A and B (On this occasion, the component force F2y acts in the centripetal direction from the periphery of the axis center P1 360 degree, facing the axis center P1, then both are matched compressing the pillar portion 16 in the centripetal direction.). That is, when the pillar portion 16 is installed in the installation space 4b, the rib for holding 11 and the projection for holding 10, the abutting end face 16b and the wall face 7a of the end wall portion 7 abut on and engage with each other such that the pillar portion 16 between the rib for holding 11 and the abutting end face 16b receives a predetermined compressive stress, such as the contact pressure F4 and the component force F2x, from the projection for holding 10 and the wall face 7a, respectively. That is, as shown in FIG. 2, if the length from the wall face 7a to the position MQ1 of the installation space 4b in the direction as shown by the arrows A and B is a length LS1 and the length from the abutting end face 16b to the position MQ2 of the pillar portion 16 in the direction as shown by the arrows A and B is a length LS2, the portion corresponding to the length LS1 of the installation space 4b elastically extends and the portion corresponding to the length LS2 of the pillar portion 16 elastically reduces when the pillar portion 16 is installed in the installation space 4b (alternatively, it may be in one of two states, that the portion corresponding to the length LS1 of the installation space 4b elastically extends or that the portion corresponding to the length LS2 of the pillar portion 16 elastically reduces.). That is, when the pillar portion 16 is taken off from the installation space 4b, the portion corresponding to the length LS1 of the installation space 4b and the portion corresponding to the length LS2 of the pillar portion 16 are both in natural state, and this length LS1 is rather smaller than the length LS2.

That is, the needle installation body 15 is attachably and detachably engaged and connected with the installation space 4b, sandwitched between the end wall portion 7 and the projection for holding 10 by a predetermined compressive stress.

As mentioned before, the sections of the rib for holding 11 and the projection for holding 10 on the plane including axis center P1 are both arc shape, as shown in FIG. 3. That is, as shown in FIG. 3, the positions MQ1, MQ2 which are abutting portions between the rib for holding 11 and the projection for holding 10 and the seal portions are formed with a width W3 smaller than any of a width W1 of the projection for holding 10 and a width W2 of the rib for holding 11 in the direction as shown by the arrows A and B which is the axis center direction of the syringe body 2. Therefore, the contact and abutment between the rib for holding 11 and the projection for holding 10 realizes in such a manner as they contact annularly along the plane perpendicular to the axis center P1 substantially in the state of line contact (FIG. 3 is a sectional view, so the state of point contact is shown). Therefore, in this syringe assembly 1, high sealing efficiency exercises in comparison with one which adopts face contact sealing.

Figure 4:
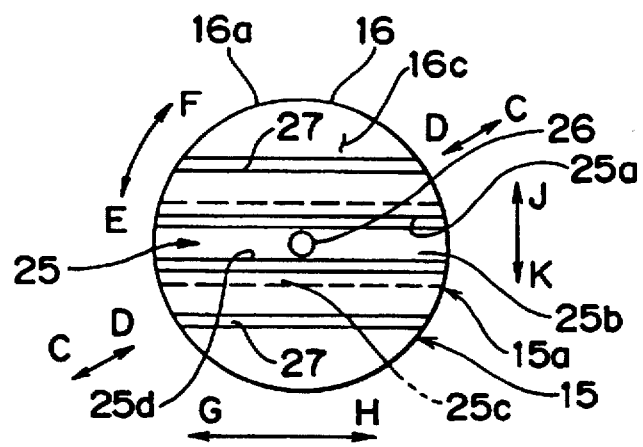
FIG. 4 is a view seen from an arrow I in FIG. 2.

Besides, an engagement groove 25 is formed for the direction as shown by the arrow A at the pillar portion 16, forming an opening portion 25a at an end face 16c of the arrow B side of the pillar portion 16. The engagement groove 25 is one penetrating the pillar portion 16 in the direction as shown by arrows G and H of the figure perpendicular to the direction as shown by the arrows A and B, as shown in FIG. 4. The engagement groove 25 is basically comprised of a through portion 25b adjacent to the opening portion 25a and a holding portion 25c communicating and connecting with the arrow A side of the through portion 25b. Between the through portion 25b and the holding portion 25c, a constriction portion 25d where the space in the direction as shown by arrows J and K of the figure perpendicular to the direction as shown by the arrows G and H is narrow from both up and down sides in the center direction (in the present embodiment, the direction for the axis center P1), is formed.

Furthermore, deformation accelerating grooves 27, 27 are provided with the pillar portion 16 on the sides of the arrow J and the arrow K of the engagement groove 25, extending from the end face 16c of the pillar portion 16 in the direction as shown by the arrow A, and these deformation accelerating grooves 27, 27 are also ones penetrating the pillar portion 16 in the directions as shown by the arrows G and H.

A needle insertion space 19 is provided with the main body 15a, formed extending in the direction as shown by the arrows A and B from the pillar portion 16 to the small pillar portion 17, forming an opening portion 19a at an end face 17a of the arrow A side of the small pillar portion 17. A medical liquid flow hole 26 formed penetrating the inside of the pillar portion 16 is provided between the end portion of the arrow B side of the needle insertion space 19 and the holding portion 25c of the engagement groove 25, communicating and connecting the needle insertion space 19 and the holding portion 25c with each other.

A needle 23 is connected with the main body 15a, being inserted in the needle insertion space 19 (the needle 23 is fixed with an adhesive or the like), and the inside of the needle 23 (that is, the space where medical liquid flows) communicates with the medical liquid flow hole 26 through the end portion of the arrow B side of the needle 23.

On the other hand, as shown in FIG. 1, the piston 39 is provided with the syringe assembly 1 (FIG. 1 is a typical sectional view of the syringe assembly 1, but a side is shown, not a section, concerning a piston main body 40, an outer pressing plate 42 and an inner pressing plate 43 mentioned hereinafter of the piston 39 for convenience.).

The piston 39 has the bar-shaped piston body 40 extending in the direction as shown by the arrows A and B. The piston body 40 is comprised such that two congruent plate portions 40a, each which is a plate shaped rectangle especially long in the direction as shown by the arrows A and B, are unitedly cross provided with each other such that the sections thereof form the shape of a cross. The width perpendicular to the direction as shown by the arrows A and B of the plate face of the plate portion 40a is almost equal to the inside diameter at the engagement rib 3b of the main cylindrical portion 3, and the piston body 40 is inserted into the main cylindrical portion 3 through the opening end 3a from the arrow A side of the piston body 40.

On each plate portion 40a of the piston body 40, notches 41 are formed from both side portions 40b, 40b of respective plate portions 40a, 40ato the direction of the axis center (that is, the axis center P1) of the piston body 40 in the shape of a wedge near the arrow A side. Four notches 41 are provided at the positions adjusted one another in the direction as shown by the arrows A and B.

The outer press plate 42, which plate face is a circular plate perpendicular to the direction as shown by the arrows A and B, is provided on the end portion side of the arrow B side of the piston body 40, being united with the piston body 40, and coaxial with the piston body 40. The diameter of the outer press plate 42 is fully bigger than the inside diameter of the main cylindrical portion 3.

As shown in FIG. 1, the inner press plate 43, which plate face is a circular plate perpendicular to the direction as shown by the arrows A and B, is provided on the end portion side of the arrow A side of the piston body 40, being united with the piston body 40 and coaxial with the piston body 40 (Therefore, the inner press plate 43 is positioned inside the main cylindrical portion 3.). The diameter of the inner press plate 43 is almost equal to the inside diameter of the main cylindrical portion 3 (Therefore, the diameter of the inner press plate 43 is bigger than the inside diameter of the engagement rib 3b of the main cylindrical portion 3.).

As shown in FIG. 1, a packing support 45, projecting in the direction as shown by the arrow A in the shape of almost cylinder is provided with the inner pressing plate 43 on the arrow A side of it. A packing 46 formed in the shape of a ring, made of flexible resin, is engaged and installed in the packing support 45. That is, the inside of the syringe body 2 can be watertightly (or airtightly) closed between the arrow A side and the arrow B side of the packing 46 by the packing 46.

Furthermore, the hub engagement portion 47 is unitedly provided on the arrow A side of the packing support 45. The hub engagement portion 47 is comprised of a pillar portion 47a extending in the directions as shown by the arrows A and B and an insertion portion 47b provided on the arrow A side of the pillar portion 47a. The insertion portion 47b, which diameter is bigger than one of the pillar portion 47a, is a semi-spherical shape. The insertion portion 47b is located facing its spherical surface 47c side to the arrow A side. The diameter of the pillar portion 47a is equal to the distance in the constriction portion 25d of the engagement groove 25 provided with the main body 15a of the needle installation body 15 in the direction as shown by the arrows J and K of the figure. The diameter of the insertion portion 47b is smaller than one of the holding portion 25c of the engagement hole 25 in the direction as shown by the arrows J and K.

The syringe assembly 1 is comprised as explained before. In order to assemble the syringe assembly 1, following steps are executed.

At first, the needle installation body 15 is installed in the syringe 100. That is, the needle installation body 15 is inserted in the direction as shown by the arrow A from the rear end side of the syringe body 2, that is, the installation side of the piston, thereafter the needle installation body 15 is inserted in the installation space 4b of the hub installation portion 4 in the direction as shown by the arrow A. By further insertion, the arrow A side portion of the rib for holding 11 of the needle installation body 15 abuts on the arrow B side portion of the projection for holding 10 of the installation space 4b (not shown). Thereafter, by strongly pressuring the needle installation body 15 against the syringe 100 in the direction as shown by the arrow A, the rib for holding 11 pressures the projection for holding 10 in the direction as shown by the arrow C. Then, by this pressuring force the installation space 4b and the like are expanded in the direction as shown by the arrow C (or since the rib for holding 11 is pressurized by the projection for holding 10 in the direction as shown by the arrow D, the pillar portion 16 is compressed in the direction as shown by the arrow D by the pressuring force), then the top end 11a of the rib for holding 11 is moved passing the position of the top end 10a of the projection for holding 10 in the direction as shown by the arrow A, and reaches a predetermined engagement and installation position, that is, the position where the rib for holding 11 and the projection for holding 10 abut on at the before-mentioned positions MQ1, MQ2. And, at the same time of the reaching the predetermined engagement and installation position, the abutting end face 16b of the pillar portion 16 and the wall face 7a of the end wall portion 7 are located at the abutting position with predetermined contact pressure F3, F4. Then, the installation of the needle installation body 15 finishes.

As mentioned before, the spacing 31 is formed between the outside peripheral face 16a of the pillar portion 16 and the inner peripheral face 4c of the installation space 4b. Besides, the outside diameter at the position of the rib for holding 11 of the pillar portion 16 is smaller than the inside diameter of the portion excluding the projection for holding 10 of the installation space 4b. Furthermore, the inside diameter at the position of the projection for holding 10 of the installation space 4b is bigger than the outside diameter of the portion excluding the rib for holding 11 of the pillar portion 16. Therefore, the contact between the pillar portion 16 and the installation space 4b when the needle installation body 15 is inserted into the installation space 4b is only contact between the rib for holding 11 and the projection for holding 10 , then frictional resistance is made extremely small between the pillar portion 16 and the installation space 4b and the installation action can be smoothly executed.

Besides, the needle 23 may be connected with the needle installation body 15 in advance of the installation of the needle installation body 15 in the syringe 100, or the needle installation body 15 in which the needle 23 is not already connected is installed in the syringe 100 and thereafter the needle 23 may be connected with the needle installation body 15.

The piston 39 is installed in the syringe 100 after the installation of the needle installation body 15 in the syringe 100, then the assembly of the syringe assembly 1 finishes.

The syringe assembly 1 assembled as mentioned before, is used, and after that, the syringe assembly 1 is discarded as follows.

At first, the syringe assembly 1 assembled is filled with an injection medium 59 in liquid state. Filling of the injection medium 59 is executed in such a manner that the piston 39 is pulled so as to generate negative pressure in the inside space 2a of the syringe body 2, and the injection medium 59 is sucked from the top end side of the needle 23. The injection medium 59 flows into the inside space 2a of the syringe body 2 through the needle 23, the medical liquid flow hole 26 in the needle installation body 15, the engagement hole 25 so as to fill therewith.

The spacing 31 is formed between the pillar portion 16 of the needle installation body 15 and the installation space 4b. But, since the rib for holding 11 of the needle installation body 15 and the projection for holding 10 of the installation space 4b abut on each other, the portion between the rib for holding 11 and the projection for holding 10 is sealed with a predetermined contact pressure, that is, with sealing pressure, then liquid does not leak.

After filling with the injection medium 59, medical liquid is injected into a patient, thereafter the syringe assembly 1 is discarded.

At first, the piston 39 and the needle installation body 15 are engaged with each other. That is, the piston 39 is further pressurized in the direction as shown by the arrow A. By this pressurizing, the insertion portion 47b of the hub engagement portion 47 of the piston 39 rushes into the through portion 25b of the engagement groove 25 of the needle installation body 15, as shown in FIG. 5. On this occasion, since the spherical face 47c is formed at the top end of the insertion portion 47b, the rushed insertion portion 47b easily passes the constriction portion 25d and reaches the holding portion 25c. Besides, the pillar portion 47a extending on the arrow B side of the insertion portion 47b exists penetrating the constriction portion 25d in the direction as shown by the arrows A and B. That is, the piston 39 and the needle installation body 15 are engaged with each other.

By acting the pressurizing force in the direction as shown by the arrow A on the insertion portion 47b, the pressurizing force in the direction as shown by the arrow A acts on the needle installation body 15 also. But, the needle installation body 15 abuts on the wall face 7a of the end wall portion 7 in the direction as shown by the arrow A in the abutting end face 16b of the pillar portion 16, then it is supported by the end wall portion 7 in the result. Therefore, even if the needle installation body 15 receives the pressurizing force, it is scarcely moved in the direction as shown by the arrow A. Then, the needle installation body 15 is not pulled out from the installation space 4b to the outside in the direction as shown by the arrow A, and it's safe.

After the piston 39 and the needle installation body 15 are engaged with each other, the piston 39 is pulled against syringe 100 in the direction as shown by the arrow B, thereby the needle installation body 15 engaged with the piston 39 through the hub engagement portion 47 and the engagement groove 25 is pulled against the syringe 100 together with the piston 39 in the direction as shown by the arrow B, as shown in FIG. 5. Then, the rib for holding 11 of the needle installation body 15 presses the projection for holding 10 in the direction as shown by the arrow C, the installation space 4b and the like are expanded in the direction as shown by the arrow C by this pressing force (or the rib for holding 11 is pressed by the projection for holding 10 in the direction as shown by the arrow D, then by this pressing force, the pillar portion 16 is compressed in the direction as shown by the arrow D). Therefore, the top end 11a of the rib for holding 11 is moved passing the position of the top end 10a of the projection for holding 10 in the direction as shown by the arrow B, and the engagement between the needle installation body 15 and the installation space 4b is released, and the needle installation body 15 and the needle 23 installed in and connected with the needle installation body 15 are inserted into the inside space 2a of the syringe body 2. The piston 39 is further pulled and the inner pressing plate 43 is pulled to the position abutting on the engagement rib 3b of the main cylindrical portion 3 of the syringe body 2 so as to stop the piston 39 , as shown in FIG. 5. On this occasion, the top end of the needle 23 is fully inserted into the inside space 2a.

As mentioned before, the spacing 31 is formed between the outside peripheral face 16a of the pillar portion 16 and the inner peripheral face 4c of the installation space 4b, the outside diameter at the position of the rib for holding 11 is smaller than the inside diameter of the portion excluding the projection for holding 10 of the installation space 4b, and the inside diameter at the position of the projection for holding 10 of the installation space 4b is bigger than the outside diameter of the portion excluding the rib for holding 11 of the pillar portion 16. Therefore, the contact between the pillar portion 16 and the installation space 4b when the needle installation body 15 is pulled from the installation space 4b is only contact between the rib for holding 11 and the projection for holding 10, then frictional resistance between the pillar portion 16 and the installation space 4b is made extremely small and pulling action can be smoothly executed. Furthermore, as soon as the top end 11a of the rib for holding 11 of the needle installation body 15 passes the position of the top end 10a of the projection for holding 10 of the installation space 4b in the direction as shown by the arrow B, the arrow A side portion of the rib for holding 11 of the needle installation body 15 abuts on the arrow B side portion of the projection for holding 10 of the installation space 4b. In this state, the contact pressure having the component of the force in the direction as shown by the arrow B acts on the rib for holding 11 from the projection for holding 10. That is, the needle installation body 15 is pressed in pulling direction or the direction as shown by the arrow B by this component of the direction as shown by the arrow B also, then the pulling action can be smoothly executed with small force. Besides, at the time of engagement between the rib for holding 11 and the projection for holding 10, the projection for holding 10 is abutted on and engaged with the rib for holding 11 and the wall face 7a is abutted on and engaged with the abutting end face 16b such that the main body 15a between the projection for holding 10 and the wall face 7a receives a predetermined compressive stress from the rib for holding 11 and the abutting end face 16b. Therefore, as soon as the engagement between the rib for holding 11 and the projection for holding 10 is released, this compressive stress is released so as to spring out the main body 15a in the direction as shown by the arrow B, thereby the needle installation body 15 can be further smoothly pulled out with smaller force.

Besides, the inner pressing plate 43 of the piston 39 is engaged with and stopped by the engagement rib 3b so as to prevent the needle 23 installed into the needle installation body 15 engaged with the piston 39 from springing to the outside the syringe body 2, by excessively pulling the piston 39 by mistake. In addition, the accident of secondary infection or the like generating from the hurt of hands and the like by the needle 23 can be prevented.

And, in such a state that the inner pressing plate 43 of the piston 39 is engaged with and stopped by the engagement rib 3b, the position of the notch 41 formed on the piston body 40 of the piston 39 is almost adjusted to the position of the opening end 3a of the syringe body 2 in the direction as shown by the arrow A and B, as shown in FIG. 5.

Subsequently, while the syringe body 2 is fixed with one hand, the piston 39 is grasped with the other hand, and as shown in FIG. 5, a force in the direction as shown by the arrow C is added to the piston 39. By adding a force in the direction as shown by the arrow C to the piston 39 with respect to the syringe body 2, bending stress is added to the piston body 40 with the engagement rib 3b and the opening end 3a of the syringe body 2 as a supporting point, and then the piston body 40 is broken in the notch 41, in which structure of the piston body 40 is relatively weak with respect to bending stress, and the piston body 40 is separated into the arrow A side portion and the arrow B side portion forming a boundary with the notch 41. Thereafter, the portion of the syringe body 2 side and the portion of the outer pressing plate 42 of the piston 39 broken and taken off are discarded.

Figure 6:
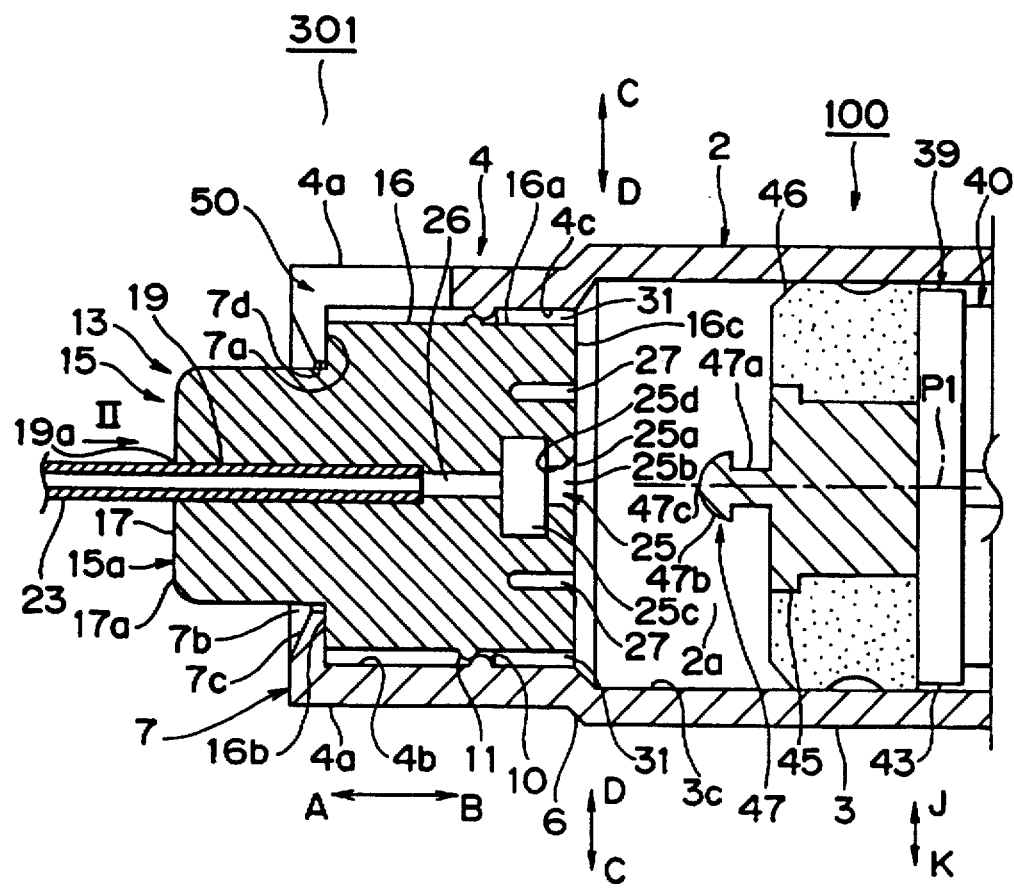
FIG. 6 is an enlarged sectional view in the portion near the installation space of an example of another syringe assembly according to the present invention.
Figure 7:
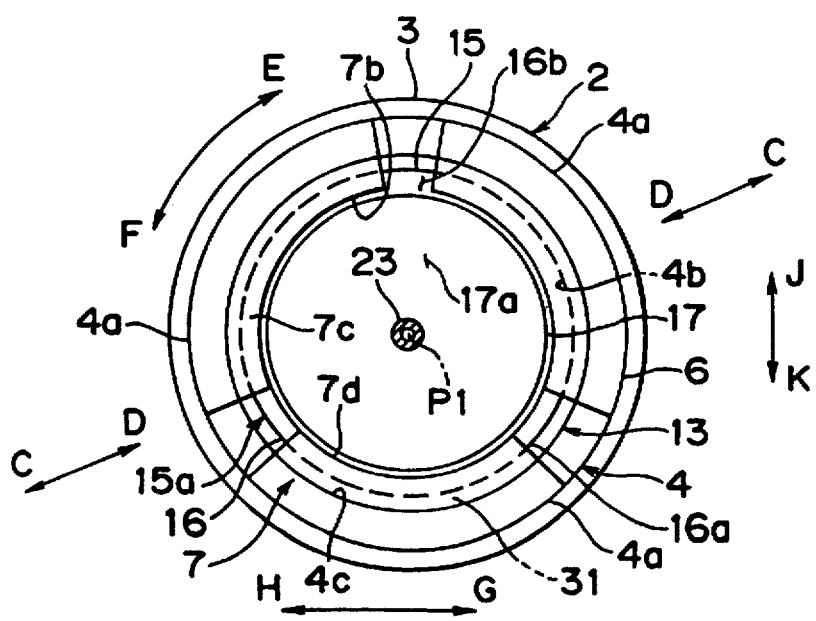
FIG. 7 is a view seen from an arrow II of FIG. 6.

In the present invention, the syringe assembly may be comprised by forming one or more slits at the periphery of a penetrating hole, such as the penetrating hole 7b. As shown in FIGS. 6 and 7, in the syringe assembly, such as the beforementioned syringe assembly 1, a plurality of slits 50 (in the present embodiment the number is three, but any number more than one is available) are provided on the top end side of the syringe body 2 so as to comprise a syringe assembly 301 which is another example of the syringe assembly of the present invention. These slits 50 are provided at an equal pitch (120 degree pitch in FIG. 7) at the periphery of the penetrating hole 7b with the axis center P1 as its center as shown in FIGS. 6 and 7. Each slit 50 divides the end wall portion 7, and furthermore the arrow A side portion of the installation portion 4 is divided into a plurality of an installation portion piece 4a (in the present embodiment the number is three). The position forming the projection for holding 10 in the installation space 4b is different from one in the case of the syringe assembly 1 above-explained (that is, is moved and located in the direction as shown by the arrow B in comparison with the case of the syringe assembly 1). The projection for holding 10 in the syringe assembly 301 is located on the arrow B side rather than the top end position on the arrow B side of these slits 50. Therefore, the rib for holding 11 of the needle installation body 15 is also located on the arrow B side in comparison with the case of the syringe assembly 1, corresponding to the position of the projection for holding 10. Furthermore, in the before-explained syringe assembly 1, the penetrating hole 7b of the end wall portion 7 is a hole which inside diameter with the axis center P1 as its center is constant in the direction as shown by the arrows A and B, but is a taper hole expanding for the direction as shown by the arrow A in the syringe assembly 301.

Since the syringe assembly 301 is comprised as mentioned before, the installation of the needle installation body 15 on the syringe body 2 can be executed from the top end side of the sryinge body 2 through the penetrating hole 7b. That is, the needle installation body 15 is installed in such a manner that the end face 16c of the arrow B side of the pillar portion 16 of the needle installation body 15 is matched with the penetrating hole 7b of the end wall portion 7 and is pressed in the direction as shown by the arrow B continuously. On this occasion, the end wall portion 7 side of the hub installation portion 4 is divided into a plurality of the installation portion piece 4a by a plurality of the slit 50 as mentioned before, by pressurizing the end wall portion 7 by the needle installation body 15, the end face 16c of the pillar portion 16 pressurizes and abuts on a hole face 7c in the shape of a taper facing the penetrating hole 7b, then an action force acts on these installation portion pieces 4a so as to elastically bend and deform these installation portion pieces 4a in the direction as shown by the arrow C. Then, with further pressurizing the needle installation body 15, each installation portion piece 4a elastically bends and deforms in the direction as shown by the arrow C and the inside diameter of the penetrating hole 7b expands.

The pillar portion 16 of the needle installation body 15 is fully inserted into the installation space 4b in such a manner that the needle installation body 15 is further pressurized in the direction as shown by the arrow B so as to elastically bend and deform the installation portion piece 4a and the inside diameter of the penetrating hole 7b is expanded to the degree of the outside diameter of the pillar portion 16 of the needle installation body 15. By doing so, the pillar portion 16 is inserted into the installation space 4b abutting the abutting end face 16b of the pillar portion 16 on the wall face 7a of the arrow B side of the end wall portion 7 with a predetermined contact pressure, and abutting the rib for holding 11 and the projection for holding 10 on each other with a predetermined contact pressure, then the installation of the needle installation body 15 finishes.

The face facing the penetrating hole 7b of the end wall portion 7 has a through surface 7d connecting with the arrow B side of the hole face 7c as well as the hole face 7c in the shape of a taper mentioned before. The through surface 7d is a curved face comprised of an inner peripheral face of a cylinder parallel extending in the direction as shown by the arrows A and B. Forming this through surface 7d extremely avoids making the top end of the arrow D side of the end wall portion 7 thin and sharp (It would be made sharp if the through surface 7d were not provided, so with only the hole face 7c). That is, the strength of the arrow D side of the end wall portion 7 is increased. Therefore, when the needle installation body 15 passes the penetrating hole 7b, the damage of the top end portion of the arrow D side of the end wall portion 7 and the insertion of an extraneous body damaged into the syringe body 2 is extremely saved, then it is convenient. Furthermore, since the through face 7d extends parallel in the directions as shown by the arrows A and B, the through face 7d serves a guide face against the needle installation body 15 when the needle installation body 15 passes the penetrating hole 7b, then the insertion is smooth and it is convenient.

In the assembly of the syringe assembly 301, the connection of the needle 23 with the needle installation body 15 and the installation of the piston 39 in the syringe body 2 is executed together with the installation of the needle installation body 15. But, these work steps are optional. For instance, the order may be the installation of the needle installation body 15, the connection of the needle 23 and next the installation of the piston 39, or the installation of the needle installation body 15, the installation of the piston 39, and next the connection of the needle 23, or the connection of the needle 23, the installation of the needle installation body 15, and next the installation of the piston 39, or the connection of the needle 23, the installation of the piston 39, and next the installation of the needle installation body 15, or the installation of the piston 39, the connection of the needle 23, and next the installation of the needle installation body 15, or the installation of the piston 39, the installation of the needle installation body 15, and next the connection of the needle 23.

In this way, in the assembly of the syringe assembly 301 having slits 50, almost portion of the assembly works (that is, all the work excluding the work of the insertion and fixing of the needle 23) is executed by pressing in the direction as shown by the arrows A and B. Then it is easy without complex work. Furthermore, since the needle installation body 15 is installed without passing the inside space 2a, the insertion of dust and the like into the inside space 2a at the time of installation work is extremely saved. Besides, in case where the installation of the needle installation body 15 is executed after the installation of the piston 39 in the syringe body 2, the insertion of dust and the like into the inside space 2a at the time of installation work of the needle installation body 15 is further saved, conveniently.

The syringe assembly 301 having slits 50 is comprised and assembled as explained before. In order to use the syringe assembly 301, and to discard after use, the steps almost similar to the syringe assembly 1 having no slit 50 in the first embodiment are executed.

Figure 8:
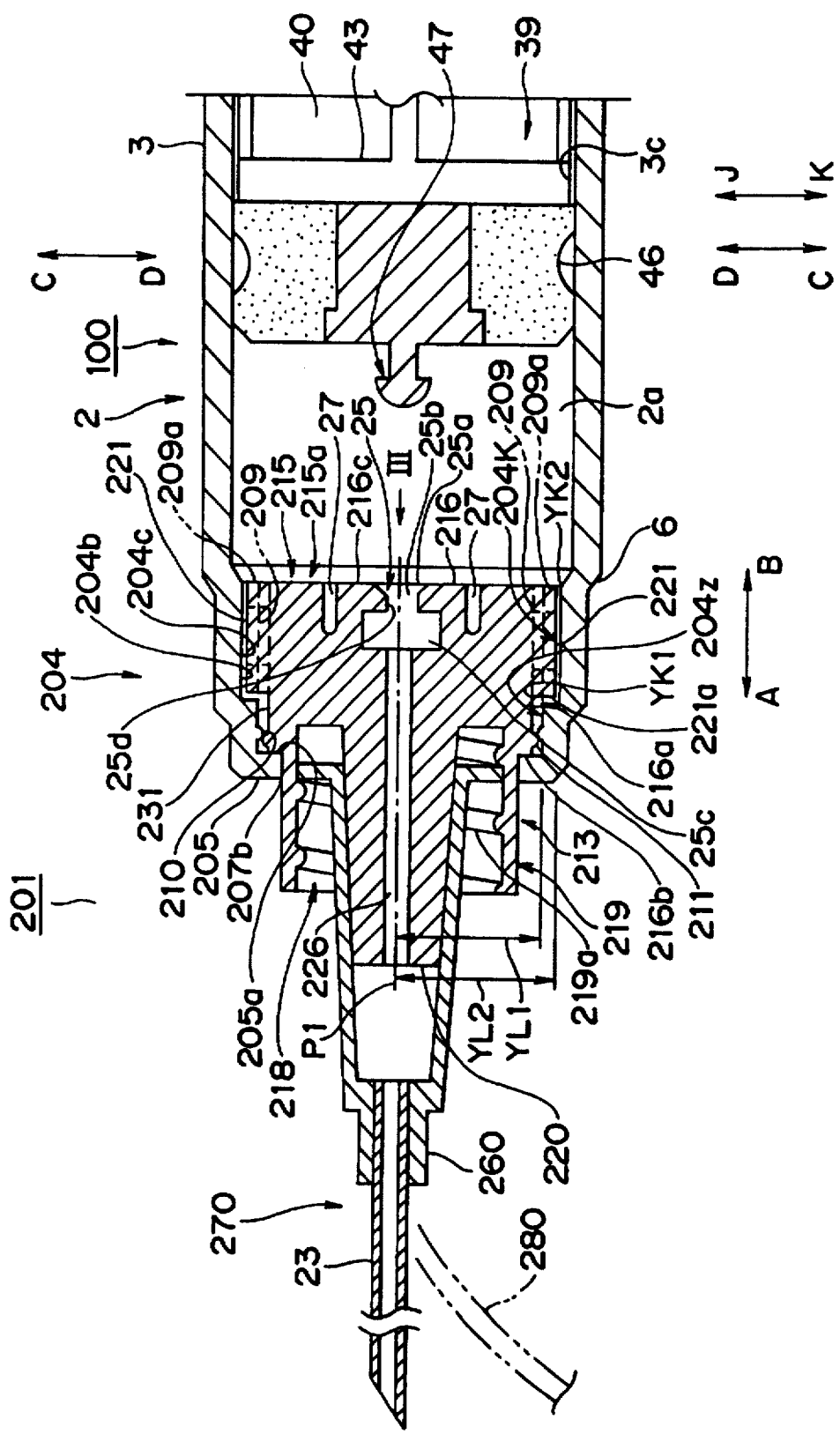
FIG. 8 is an enlarged sectional view in the portion near the installation space of an example of another syringe assembly according to the present invention.
Figure 9:
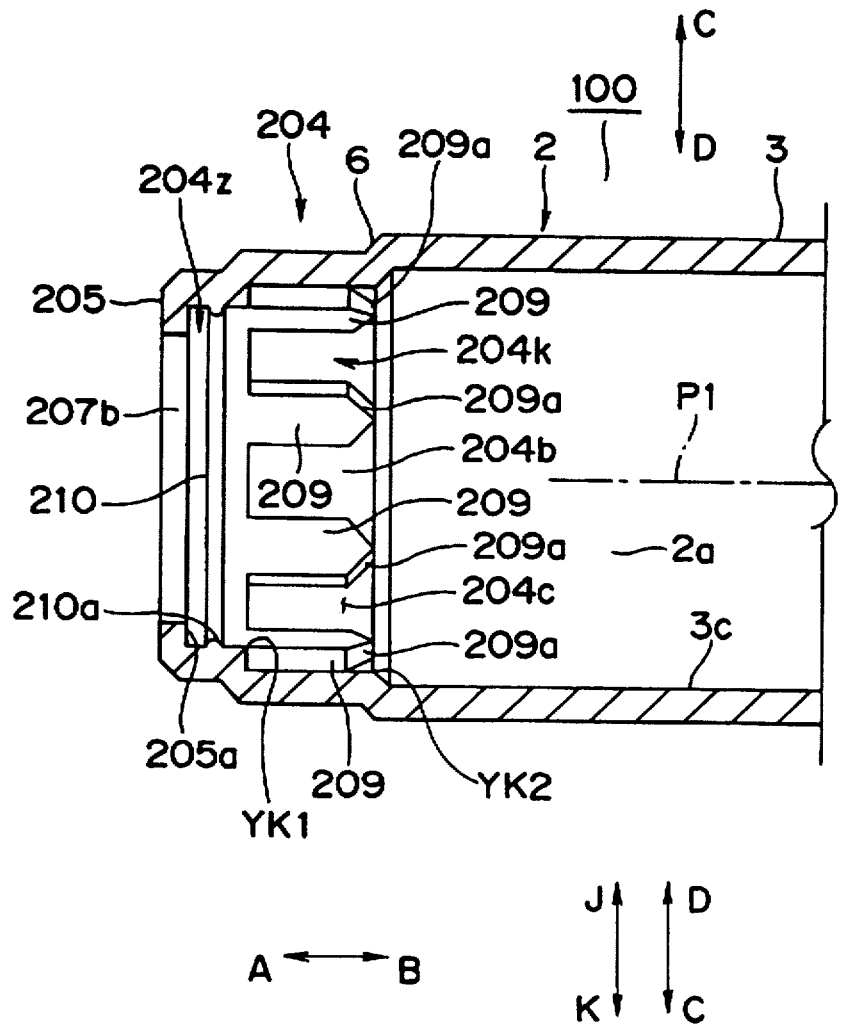
FIG. 9 is a sectional view showing only a syringe body side of the syringe assembly as shown in FIG. 8.

On the other hand, as the syringe assembly according to the present invention, so-called LEUR-LOCK type syringe assembly may be adopted excluding such one as the syringe assemblies 1, 301 before-explained where a hub, such as the needle installation body 15, directly connected a needle body, such as the needle 23, is installed in the installation hole 4b of the syringe body 2. For instance, a syringe assembly 201 as shown in FIGS. 8 through 11 is possible. The syringe assembly 201 is different from the before-mentioned syringe assembly I in the liquid flow thin tube holding member (the needle installation body 15 in the syringe assembly 1) and the holding member installation space (the installation space 4b in the syringe assembly 1) in its structure (other portions are comprised in a similar way). That is, as shown in FIGS. 8 and 9, the main cylindrical portion 3 formed in the cylindrical shape is provided with the syringe body 2 of the syringe assembly 201, similar to the syringe assembly 1. On the arrow A side of the main cylindrical portion 3, an installation portion 204 in the shape of a cylinder is formed extending in the direction as shown by the arrow A, unitedly connecting through the taper 6 in the shape of a funnel. The installation portion 204 has an installation space 204b in the shape of a cylinder therein. At the top end of the arrow A side of the installation portion 204, an end wall portion 205 perpendicular to the direction as shown by the arrows A and B (the direction parallel to the axis center P1) is formed projecting in the direction for the axis center P1 of the syringe body 2, that is, in the direction as shown by the arrow D. A penetrating hole 207b open in almost circular shape is provided with the end wall portion 205, penetrating the end wall portion 205 in the direction as shown by the arrows A and B, communicating the installation space 204b and the outside of the syringe body 2 with each other in the direction as shown by the arrows A and B. At the position on the arrow B side of the end wall portion 205, on the inner peripheral face 204c side of the installation space 204b, a projection for holding 210 is provided, as shown in FIG. 9. That is, the projection for holding 210 is formed in the shape of a rib projecting from the inner peripheral portion of the installation space 204b in the direction as shown by the arrow D of the figure. The projection for holding 210 is basically annularly formed in the shape of a stripe along the inner peripheral portion of the installation space 204b, and along the plane perpendicular to the direction as shown by the arrows A and B. The section of the projection for holding 210 on the plane including the axis center P1 is an arc shape having a top end 210a where the distance from the axis center P1 is minimum, similar to the top end 10a, in a similar way to the projection for holding 10 of the syringe assembly 1 before-mentioned.

Concerning the installation space 204b, the portion of the inner peripheral face 204c of the installation space 204b on the arrow A side from a position YK1 is a front installation portion 204z with the position YK1 on the arrow B side rather from the projection for holding 210 as a boundary, and the other portion of it between the position YK1 and a position YK2 which is a boundary with the taper 6 is a rear installation portion 204k. A basic distance YL1 in the front installation portion 204z from the inner peripheral face 204c of the installation space 204b to the axis center P1 (that is, the distance in the portion excluding the projection for holding 210 from the inner peripheral face 204c to the axis center P1) is smaller than a basic distance YL2 in the rear installation portion 204k from the inner peripheral face 204c of the installation space 204b to the axis center P1.

Figure 11:
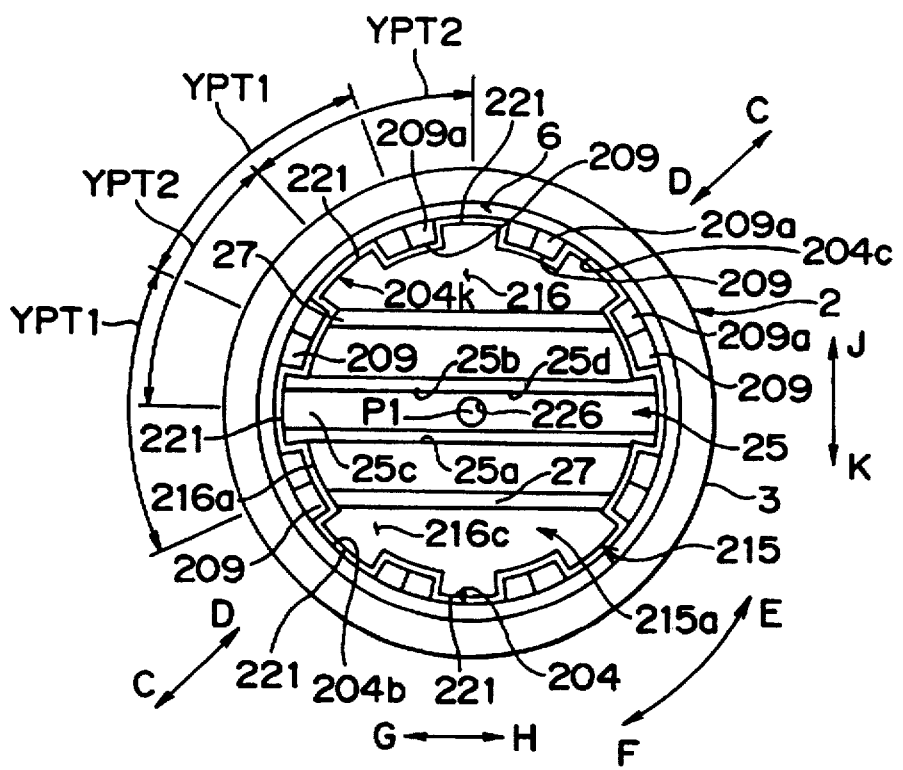
FIG. 11 is a view seen from an arrow III of FIG. 8.

As shown in FIGS. 8 and 9, a plurality of a stopper portion 209 each comprised of a projection body is formed projecting for the axis center P1 at the rear installation portion 204k on the inner peripheral face 204c side of the installation space 204b. Each stopper portion 209 is formed in the shape of a stripe extending in the direction as shown by the arrows A and B between the positions YK1 and YK2. These stopper portions 209 (the number is eight as shown in FIG. 11 in the present embodiment) are located at a predetermined pitch YPT1 with the axis center P1 as its center (45 degrees pitch in the present embodiment), as shown in FIG. 11. The distance from each stopper portion 209 to the axis center P1 is equal to the basic distance YL1 in the front installation portion 204z from the inner peripheral face 204c of the installation space 204b to the axis center P1, that is, the end portion of the arrow D side of each stopper portion 209 smoothly communicates in the direction as shown by the arrows A and B with the inner peripheral face 204c near the position YK1, which is the inner peripheral face 204c of the installation space 204b in the front installation portion 204z. An end portion 209a on the arrow B side of each stopper portion 209 is a wedge shape, being sharp in the direction as shown by the arrow B.

Figure 10:
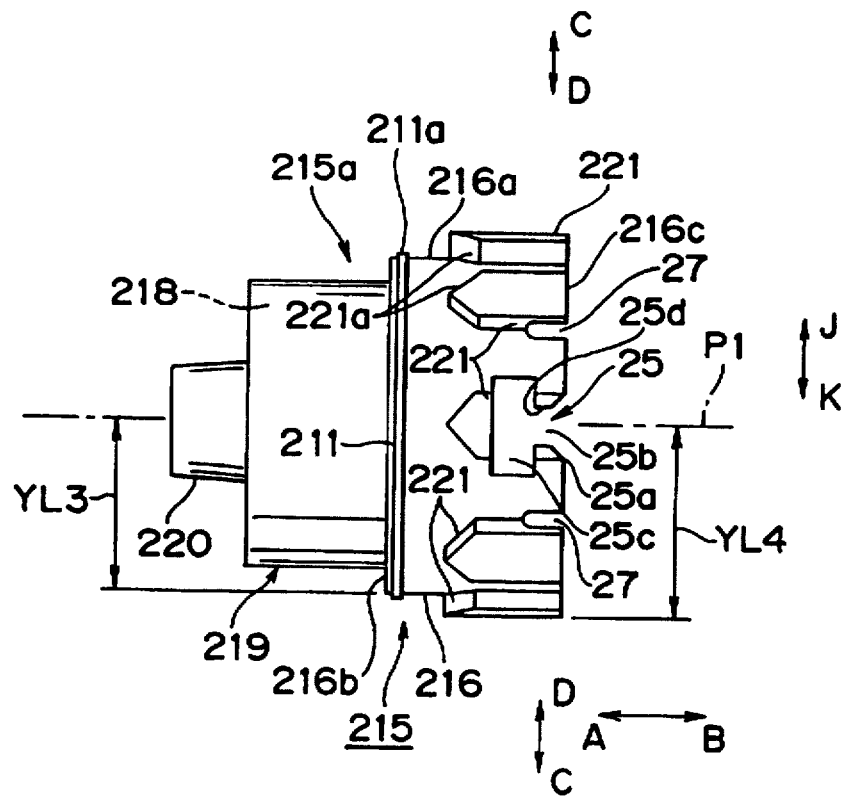
FIG. 10 is a side view showing only needle installation body side of the syringe assembly as shown in FIG. 8.

On the other hand, as shown in FIG. 8, a needle installation unit 213 is installed in the installation space 204b. The needle installation unit 213 has a needle installation body 215 inserted and installed in the installation space 204b. The needle installation body 215 has a main body 215a basically cylindrically shaped, linearly inserted in the installation space 204b from the piston installation side (that is, the inside space 2a side of the syringe body 2) in the direction as shown by the arrow A and linearly pulled from the installation space 204b into the inside space 2a of the syringe body 2 in the direction as shown by the arrow B, as shown in FIG. 8 and FIG. 10. Besides, the main body 215a has a pillar portion 216 in the shape of a cylinder. On the outer peripheral face 216a side of the pillar portion 216, a rib for holding 211 is formed projecting in the direction as shown by the arrow C. The rib for holding 211 is a stripe in annular shape along the plane perpendicular to the direction as shown by the arrows A and B parallel to the axis center of the pillar portion 216, that is, the axis center of the main body 215a (which corresponds with the axis center P1 of the syringe body 2 in the case of the present embodiment), and is formed along the outer peripheral face 216a. The section of the rib for holding 211 on the plane including the axis center P1 is an arc having a top end 211a similar to the top end 11a where distance from the axis center P1 is maximum, similar to the before-mentioned rib for holding 11 of the syringe assembly 1.

On the arrow A side of the pillar portion 216, a cylindrical portion 219, coaxial with the pillar portion 216, which diameter is smaller than the pillar portion 216, is unitedly provided. The cylindrical portion 219 extends in the direction as shown by the arrow A passing the inside of the installation space 204b and the penetrating hole 207b. Besides, the outside diameter of the cylindrical portion 219 is smaller than the inside diameter in the front installation portion 204z of the installation space 204b and is rather smaller than the inside diameter of the penetrating hole 207b. The outside diameter of the portion corresponding to the front installation portion 204z of the pillar portion 216 is bigger than the outside diameter of the cylindrical portion 219 and the inside diameter of the penetrating hole 207b. Then, at the end portion of the arrow A side of the pillar portion 216, an abutting end face 216b in annular shape is formed enclosing the cylindrical portion 219 by the difference of the diameter of the pillar portion 216 and the cylindrical portion 219. In the state that the needle installation unit 213 is installed in the installation space 204b, the abutting end face 216b is located abutting on a wall face 205a of the arrow B side of the end wall portion 205 with a predetermined contact pressure, as shown in FIG. 8. In this state, the rib for holding 211 abuts on the projection for holding 210 of the installation space 204b with a predetermined contact pressure. This abutment is similar to one between the rib for holding 11 and the projection for holding 10 in the before-mentioned syringe assembly 1 (see FIG. 3), then the needle installation body 215 is attachably and detachably engaged and connected with the installation space 204b, being engaged and sandwitched between the end wall portion 205 and the projection for holding 210 with a predetermined compressive force.

Concerning the pillar portion 216, as shown in FIG. 8 and FIG. 10, a basic distance YL3 from the axis center P1 to the outer peripheral face 216a in the direction as shown by the arrows C and D is rather smaller than the distance YL1 from the axis center P1 to the inner peripheral face 204c side in the installation space 204b in the direction as shown by the arrows C and D. Then, in the state that the main body 215a is engaged with the installation space 204b, a space in the direction as shown by the arrows C and D is formed as a spacing 231 between the inner peripheral face 204c excluding the rib for holding 211 in the front installation portion 204z of the installation space 204b and the outer peripheral face 216a of the pillar portion 216, and between the end portion of the arrow D side of the stopper portion 209 in the rear installation portion 204k of the installation space 204b and the outer peripheral face 216a of the pillar portion 216.

As shown in FIGS. 8, 10 and 11, at the portion corresponding to the rear installation portion 204k of the outer peripheral face 216a of the pillar portion 216, a plurality of a peripheral direction abutting portion 221 are provided projecting in the direction as shown by the arrow C. Each peripheral direction abutting portion 221 is formed in the stripe shape extending in the direction as shown by the arrows A and B. These peripheral direction abutting portions 221 (the number is eight as shown in FIG. 11 in the present embodiment) are located at a pitch YPT2 with the axis center P1 as its center, the same pitch as the before-mentioned predetermined pitch YPT1 (45 degrees pitch in the present embodiment), as shown in FIG. 11. As shown in FIGS. 8 through 10, a distance YL4 from the end portion of the arrow C side of each peripheral direction abutting portion 221 to an axis center XP1 is rather smaller than the basic distance YL2 from the inner peripheral face 204c excluding the position of each stopper 209 to the axis center P1 of the installation space 204b in the rear installation portion 204k. In the state that the needle installation unit 213 is installed in the installation space 204b, each peripheral direction abutting portion 221 is located sandwitched between the stopper portions 209, 209 adjacent to the peripheral direction, as shown in FIG. 8 and FIG. 11. Besides, an end portion 221a of the arrow A side of each peripheral direction abutting portion 221 is a wedge shape being sharp in the direction as shown by the arrow A.

In order to install the needle installation body 215 of the needle installation unit 213 in the installation space 204b, the needle installation body 215 is inserted into the syringe body 2 from the piston installation side which is the inside space 2a side, and inserted into the installation space 204b in the direction as shown by the arrow A so as to engage through the projection for holding 210 and the rib for holding 211. When the needle installation body 215 is inserted into the installation space 204b, the engagement between the peripheral direction abutting portion 221 and the stopper portion 209 is smooth, conveniently since the end portion 221a of the arrow A side of each peripheral direction abutting portion 221 is a wedge shape being sharp in the direction as shown by the arrow A and the end portion 209a of the arrow B side of each stopper portion 209 is a wedge shape being sharp in the direction as shown by the arrow B.

As explained heretofore, in the state that the needle installation unit 213 is installed in the installation space 204b, each stopper portion 209 and each peripheral direction abutting portion 221 are free to abut on each other in the peripheral direction. Then, even if the needle installation unit 213 would be about to rotate in the peripheral direction with respect to the syringe body 2, each stopper portion 209 and each peripheral direction abutting portion 221 would abut on in the peripheral direction, then the rotation will be prevented. Therefore, when a hub 260 mentioned hereinafter is installed on the needle installation body 215 by screwing, the needle installation body 215 is prevented from rotating with the hub 260 in the installation space 204b so as to make the installation of the hub 260 easy.

As shown in FIG. 8, a screw hole for hub 218, being capable installing the hub 260 in the cone shape on the main body 215a by screwing, which is adopted in a LUER-LOCK type syringe assembly, is formed inside of the cylindrical portion 219, forming a screw thread 219a on the inner peripheral face side of the cylindrical portion 219.

Furthermore, on the arrow A side in the figure which is the top end side of the main body 215a, a taper for hub 220 in the shape of a cylinder is unitedly provided projecting and extending in the direction as shown by the arrow A, coaxial with the pillar portion 216 on the arrow A side of the pillar portion 216. The taper for hub 220 is located in the center of the inside of the cylindrical portion 219. The hub 260 is installed on the main body 215a through these screw hole for hub 218 and the taper for hub 220. The needle 23 which is a needle main body is connected with this hub 260, and a needle unit 270 is comprised of these hub 260 and the needle 23 (Therefore, the syringe assembly 201 is one for injection of medical liquid or blood collecting).

In place of the needle unit 270, another liquid flow thin tube member unit may be adopted. For instance, the liquid flow thin tube member unit may be comprised by connecting the hub 260 with a tube 280 for medical liquid transport (shown with the two-dot long and two short dashes line of FIG. 8) (In this case, the syringe assembly 201 is used as one connected with a tube for intravenous drip or blood collecting).

As shown in FIG. 8, similar to the pillar portion 16 of the syringe assembly 1, the engagement groove 25 is formed for the direction as shown by the arrow A at the pillar portion 216 forming the opening portion 25a at an end face 216c of the arrow B side thereof. The engagement groove 25 is a groove penetrating the pillar portion 216 in the direction as shown by the arrows G and H of the figure perpendicular to the direction as shown by the arrows A and B, as shown in FIG. 11. The engagement groove 25 is basically comprised of the through portion 25b adjacent to the opening portion 25a and the holding portion 25c communicating and connecting with the arrow A side of the through portion 25b.

Between the through portion 25b and the holding portion 25c, the constriction portion 25d, where the distance in the direction as shown by the arrows J and K in the figure perpendicular to the direction as shown by the arrows G and H is narrow from the both sides of up and down in the center direction (the direction for the axis center P1 in the present embodiment), is formed. Furthermore, the deformation accelerating grooves 27, 27 are provided with the pillar portion 216 on the arrow J side and the arrow K side of the engagement groove 25 , extending from the end face 216c of the pillar portion 216 in the direction as shown by the arrow A. These deformation accelerating grooves 27, 27 are also grooves penetrating the pillar portion 216 in the direction as shown by the arrows G and H.

A medical liquid flow hole 226 formed extending over the pillar portion 216 and the taper for hub 220 in the direction as shown by the arrows A and B is provided with the main body 215a, communicating and connecting the outside of the top end side of the taper for hub 220 and the holding portion 25c of the engagement groove 25 with each other.

Since the needle installation body 215 which is the liquid flow thin tube holding member and the installation space 204b which is the holding member installation space of the syringe assembly 201 are comprised as explained heretofore, the assembly and the disposal after use of the syringe assembly 201 is similar to the syringe assembly 1 mentioned before.

Figure 12:
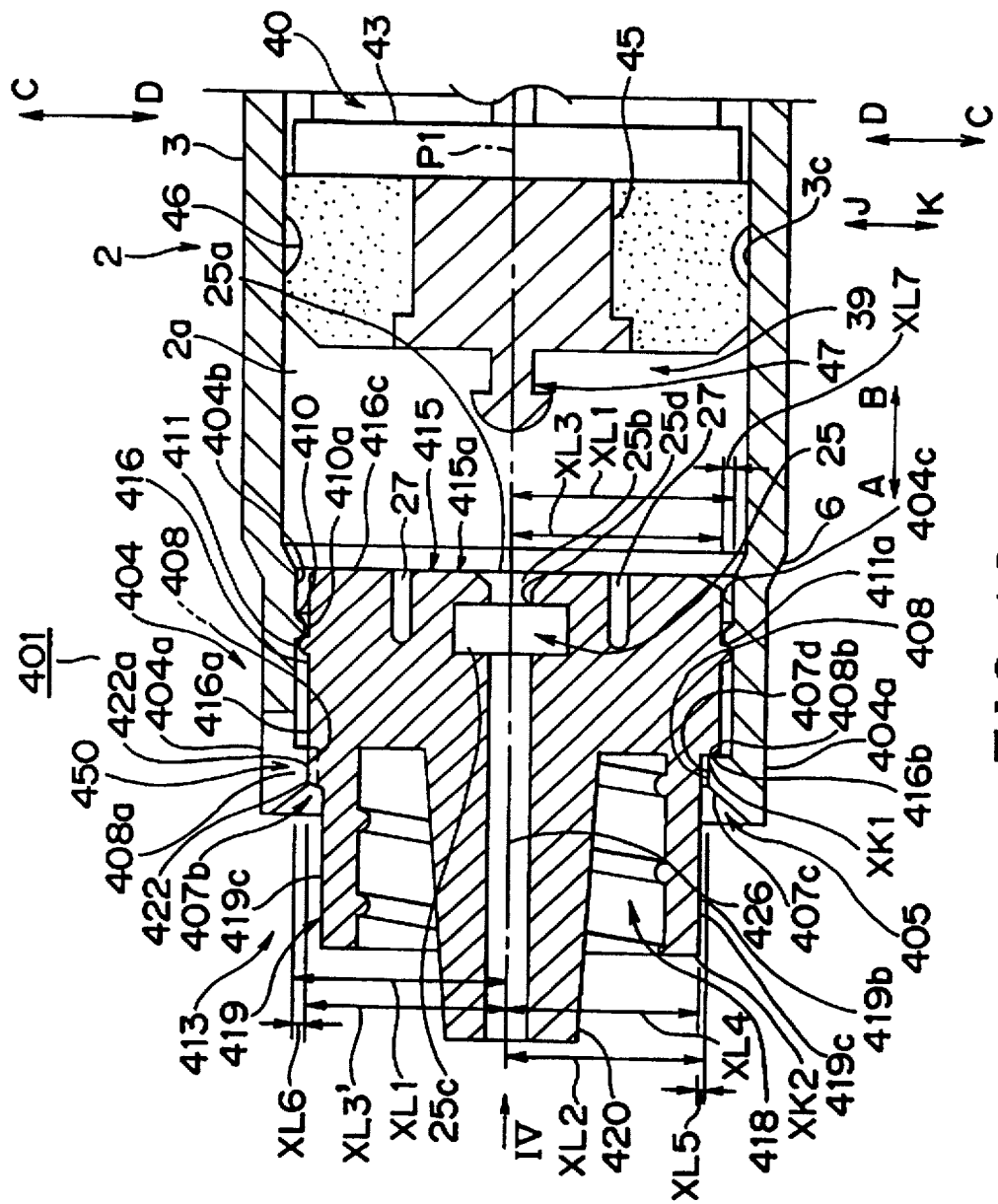
FIG. 12 is an enlarged sectional view in the portion near the installation space of an example of another syringe assembly according to the present invention.
Figure 13:
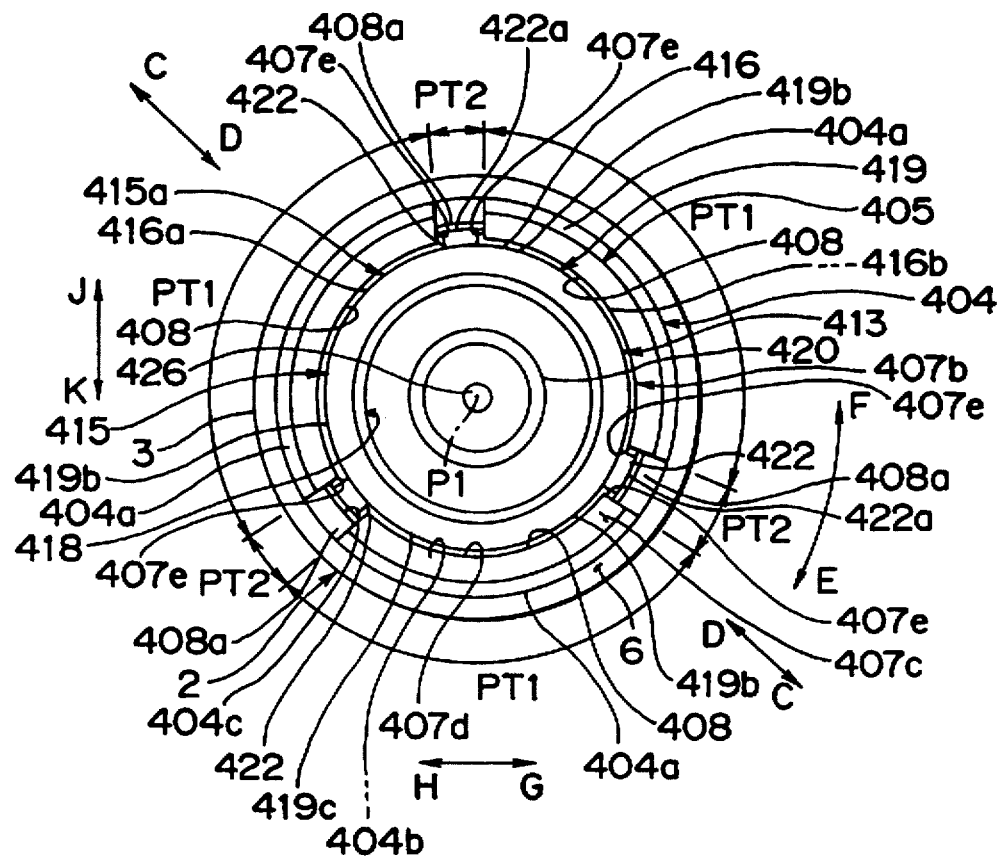
FIG. 13 is a view seen from an arrow IV of FIG. 12.

In the LUER-LOCK type syringe assembly, one having one or more than one slits at the periphery of a penetrating hole, such as the penetrating hole 207b, may be adopted. For instance, a syringe assembly 401 as shown in FIGS. 12 and 13, is possible. The syringe assembly 401 is different from the before-mentioned syringe assembly 201 in the liquid flow thin tube holding member (the needle installation body 215 in the syringe assembly 201) and the holding member installation space (the installation space 204b in the syringe assembly 201) in its structure (other portions are comprised in almost similar way). That is, as shown in FIGS. 12 and 13, the main cylindrical portion 3 cylindrically formed is provided with the syringe body 2 of the syringe assembly 401, similar to the syringe assembly 201. On the arrow A side of the main cylindrical portion 3, an installation portion 404 cylindrically shaped is formed extending in the direction as shown by the arrow A, unitedly connecting, through the taper 6 in the shape of a funnel. The installation portion 404 has a cylindrically shaped installation space 404b therein-side. At the top of the arrow A side of the installation portion 404, an end wall portion 405 perpendicular to the direction as shown by the arrows A and B (the direction parallel to the axis center P1) is formed projecting in the direction for the axis center P1 of the syringe body 2, that is, in the direction as shown by the arrow D. A penetrating hole 407b opened in almost circular shape penetrating the end wall portion 405 in the direction as shown by the arrows A and B is provided with the end wall portion 405 communicating the installation space 404b and the outside of the syringe body 2 with each other in the direction as shown by the arrows A and B. At the end portion of the arrow D side of the end wall portion 405, a hole face 407c and a through surface 407d are formed, facing the penetrating hole 407b, similar to the hole face 7c and the through surface 7d of the before-mentioned syringe assembly 301.

The end wall portion 405 is comprised of three projecting bodies 408 extending in the arc shape at a predetermined pitch PT1 with the axis center P1 as its center (for instance, the pitch is 105 degrees in FIG. 13). A lacking portion 408a extending in arc shape is formed between respective projecting bodies 408, 408 at a predetermined pitch PT2 with the axis center P1 as its center (for instance, the pitch is 15 degrees in FIG. 13). That is, three projecting bodies 408 are located in the direction as shown by arrows E and F in the figure which is the peripheral direction with the axis center P1 as its center.

As shown in FIGS. 12 and 13, three slits 450 are formed at the installation portion 404, dividing the arrow A side of the installation portion 404 into three installation portion pieces 404a with the axis center P1 as its center. These respective slits 450 are formed making lacking portion in the installation portion 404 extending in the arc shape at the predetermined pitch PT2 with the axis center P1 as its center (that is, the same pitch as the pitch PT2 of the lacking portion 408a before-mentioned). Besides, these respective slits 450 are formed at the positions corresponding to and matching with each lacking portion 408a of the before-mentioned end wall portion 405. That is, each slit 450 is located between respective projecting bodies 408, 408 of the end wall portion 405.

A projection for holding 410 of the arc shaped section having a top end 410a where the distance from the axis center P1 is minimum, similar to the projection for holding 210 in the syringe assembly 201, is an annular stripe along the plane perpendicular to the direction as shown by the arrows A and B, at the position of the arrow B side with respect to the three slits 450 before-mentioned of an inner peripheral face 404c, on the inner peripheral face 404c side of the installation space 404b.

On the other hand, as shown in FIG. 12 and FIG. 13, a needle installation unit 413 is installed in the installation space 404b (In FIGS. 12 and 13, the hub, such as the hub 260, and the needle, such as the needle 23, of the needle installation unit 413 are omitted for the convenience of explanation). The needle installation unit 413 has a needle installation body 415 inserted and installed in the installation space 404b. The needle installation body 415 has a main body 415a shaped basically cylindrically, which is linearly inserted into the installation space 404b through the penetrating hole 407b in the direction as shown by the arrow B and is linearly pulled from the installation space 404b in the inside space 2a of the syringe body 2 in the direction as shown by the arrow B.

Furthermore, the main body 415a has a pillar portion 416 in the shape of a cylinder. A rib for holding 411 of the arc shaped section having a top end 411a where the distance from the axis center P1 is maximum, formed annular stripe along the plane perpendicular to the direction of the axis center of the pillar portion 416, that is, in the direction of the axis center of the main body 415a (corresponds with the axis center P1 in the case of the present embodiment), that is, in the direction as shown by the arrows A and B in the figure, is formed along an outer peripheral face 416a on the outer peripheral face 416a side of the pillar portion 416, similar to the rib for holding 211 of the syringe assembly 201. This rib for holding 411 is attachably and detachably contacted and engaged with the projection for holding 410 of the installation space 404b with a predetermined contact pressure, similar to the case of the syringe assembly 201. By this engagement the needle installation body 415 is attachably and detachably engaged and connected with the installation space 404b.

As shown in FIG. 12, concerning the pillar portion 416, a distance XL3 from the axis center P1 to the outer peripheral face 416a in the direction as shown by the arrows C and D (that is, the half size of the outside diameter) is rather smaller than a distance XL1 from the axis center P1 to the inner peripheral face 404c in the direction as shown by the arrows C and D (that is, the half size of the inside diameter) in the installation space 404b. Then, in the state the main body 415a is engaged with the installation space 404b, a distance XL7 in the direction as shown by the arrows C and D is formed as a spacing between the inner peripheral face 404c of the installation space 404b and the outer peripheral face 416a of the pillar portion 416.

On the other hand, on the arrow A side of the figure which is the top end side of the main body 415a a cylindrical portion 419 in the shape of a cylinder is unitedly provided on the arrow A side of the pillar portion 416, extending in the direction as shown by the arrow A being coaxial with the pillar portion 416, opening in the direction as shown by the arrow A, as shown in FIG. 12. The cylindrical portion 419 extends in the direction as shown by the arrow A passing from the inside of the installation space 404b to the end wall portion 405 and the through hole 407b. Concerning the cylindrical portion 419, a distance XL4 from the axis center P1 to an outer peripheral face 419c of the cylindrical portion 419 in the direction as shown by the arrows C and D (that is, the half size of the outside diameter) is rather smaller than a distance XL2 from the axis center P1 to the through face 407d in the end wall portion 405 of the installation space 404b in the direction as shown by the arrows C and D (that is, the half size of the inside diameter). That is, in the state the needle installation body 415 is engaged with the installation space 404b, a distance XL5 in the direction as shown by the arrows C and D as a spacing is formed between the end wall portion 405 and the outer peripheral face 419c of the cylindrical portion 419.

Inside of the cylindrical portion 419, a screw hole for hub 418 similar to the screw hole for hub 218 of the syringe assembly 201 is formed, and furthermore, on the arrow A side of the figure which the top end side of the main body 415a a taper for hub 420 similar to the taper for hub 220 of the syringe assembly 201 is formed on the arrow A side of the pillar portion 416.

On the other hand, an abutting end face 416b almost annularly located, is formed at the end portion of the arrow A side of the pillar portion 416 by the difference between the distance XL3 of the pillar portion 416 and the distance XL4 of the cylindrical portion 419. The abutting end face 416b is located abutting on and contacting with a side face 408b of the arrow B side of each projecting body 408 of the end wall portion 405 with a predetermined contact pressure. On this occasion, three projecting bodies 408 of the end wall portion 405 are formed extending in the arc shape at the predetermined pitch PT1 with the axis center P1 as its center, as explained before, and the lacking portion 408a is formed extending in the arc shape at the predetermined pitch PT2 with the axis center P1 as its center between respective projecting bodies 408, 408. Since the abutting end face 416b is formed corresponding to these three projecting bodies 408, the abutting end face 416b is comprised of three portions almost annularly located and each portion is formed extending in the arc shape at the pitch PT1 with the axis center P1 as its center. And, the portions excluding the abutting end face 416b extending in the arc shape at the predetermined pitch PT2 with the axis center P1 as its center are respectively provided between these respective portions.

An interference preventing face 419b is from a position XK1 adjacent to the abutting end face 416b to a top end position XK2 of the main body 415a (that is, the top end position of the arrow A side of the cylindrical portion 419) of the outer peripheral face 419c of the cylindrical portion 419. That is, since the abutting end face 416b is comprised of three portions corresponding to the three projecting bodies 408, the interference preventing face 419b is also comprised of three portions corresponding to the three projecting bodies 408.

Furthermore, a projection portion 422 is formed projecting in the direction as shown by the arrow A rather than the position of the abutting end face 416b at the portion excluding the abutting end face 416b of the end portion of the arrow A side of the pillar portion 416, that is, at the three portions extending in the arc shape at the pitch PT2, positioned between the three portions extending in the arc shape at the predetermined pitch PT1, comprising the abutting end face 416b. Each projection portion 422 projects in the direction as shown by the arrow C rather than the outer peripheral face 419c of the cylindrical portion 419. A distance XL3' from the axis center P1 to an end face 422a of the arrow C side of the projection portion 422 in the direction as shown by the arrows C and D is almost equal to the distance XL3 from the axis center P1 to the outer peripheral face 416a in the direction as shown by the arrow C and D concerning the pillar portion 416. That is, the distance XL3' is rather smaller than the distance XL1 from the axis center P1 to the inner peripheral face 404c in the direction as shown by the arrows C and D in the installation space 404b (in the present embodiment, the distance XL3 and the distance XL3' are almost equal). Then, in the state the needle installation body 415 is engaged with the installation space 404b, a distance XL6 in the direction as shown by the arrows C and D is formed as a space between the end portion 422a of the projection portion 422 and the inner peripheral face 404c of the installation space 404b.

Since each projection portion 422 is located corresponding to each lacking portion 408a of the end wall portion 405, each projection portion 422 is located between the respective projecting bodies 408, 408 of the end wall portion 405. That is, if the peripheral direction with the axis center P1 as its center is the direction as shown by the arrows E and F in the figure and the end faces of the arrow E side and the arrow F side in each projecting body 408 are peripheral direction abutting faces 407e, 407e, each projection portion 422 is located between the peripheral direction abutting faces 407e, 407e of respective projecting bodies 408, 408. Therefore, the rotation of each projection portion 422 in the direction as shown by the arrows E and F with respect to the installation space 404b, that is, the rotation of the needle installation body 415 in the direction as shown by the arrows E and F with respect to the installation space 404b is prevented by abutting these projection portions 422 on the peripheral direction abutting face 407e of each projecting body 408.

The engagement groove 25 is formed at the pillar portion 416 for the direction as shown by the arrow A forming the opening portion 25a at an end face 416c of the arrow B side thereof, similar to the case of the syringe assembly 201. The engagement groove 25 is a groove penetrating the pillar portion 416 in the direction perpendicular to the direction as shown by the arrows A and B. The engagement groove 25 is basically comprised of the through portion 25b adjacent to the opening portion 25a and the holding portion 25c communicating and connecting with the arrow A side of the through portion 25b. The constriction portion 25d is formed between the through portion 25b and the holding portion 25c. Furthermore, the deformation accelerating grooves 27, 27 are provided with the pillar portion 416 near the engagement groove 25 , extending from the end face 416c of the pillar portion 416 in the direction as shown by the arrow A. These deformation accelerating grooves 27, 27 are also grooves penetrating the pillar portion 416 in the direction perpendicular to the direction as shown by the arrows A and B.

A medical liquid flow hole 426 is provided with the main body 415a being formed extending over-the pillar portion 416 and the taper for hub 420 in the direction as shown by the arrows A and B so as to communicate and connect the outside of the top end side of the taper for hub 420 and the holding portion 25c of the engagement groove 25 with each other.

Since the syringe assembly 401 is comprised as explained heretofore, the installation of the needle installation body 415 in the syringe body 2 can be executed from the top end side of the syringe body 2 through the through hole 407b. That is, the end face 416c of the arrow B side of the pillar portion 416 of the needle installation body 415 is matched with the through hole 407b of the end wall portion 405 and is pressed in the direction as shown by the arrow B continuously so as to install the needle installation body 415. On this occasion, the end wall portion 405 side of the hub installation portion 404 is divided into a plurality of installation portion piece 404a by a plurality of the slit 450, as mentioned before. And, by pressing the end wall portion 405 with the needle installation body 415, the end face 416c of the pillar portion 416 presses and abuts on the tapered hole face 407c facing the through hole 407b. Therefore, an action force acts on these installation portion pieces 404a so as to elastically bend and deform these installation portion pieces 404a in the direction as shown by the arrow C. Then, as the needle installation body 415 is further pressed, each installation portion piece 404a elastically bends and deforms in the direction as shown by the arrow C and the inside diameter of the through hole 407b is broadened.

The pillar portion 416 of the needle installation body 415 is completely inserted into the installation space 404b while the needle installation body 415 is being pressed in the direction as shown by the arrow B so as to elastically bend and deform the installation portion piece 404a and to broaden the inside diameter of the through hole 407b to the degree of the outside diameter of the pillar portion 416 of the needle installation body 415. By doing so, the pillar portion 416 is inserted into the installation space 404b, abutting the abutting end face 416b of the pillar portion 416 on the side face 408b of the arrow B side of the end wall portion 405 with a predetermined contact pressure and abutting the rib for holding 411 and the projection for holding 410 on each other with a predetermined contact pressure. Then, the installation of the needle installation body 415 finishes. On this occasion, each projection portion 422 of the needle installation body 415 is located so as to fit the lacking portion 408a between the projecting bodies 408, 408 of the installation space 404b side.

In this way, the needle installation body 415 is installed without passing the inside space 2a in the assembly of the syringe assembly 401 having the slits 450. Therefore, the insertion of dust or the like into the inside space 2a at installation operation is extremely saved.

The syringe assembly 401 having the slits 450 is comprised and assembled as explained before. The use of the syringe assembly 401 and its disposal after use is similar to the syringe assembly 201 having no slit 450.

Figure 14:
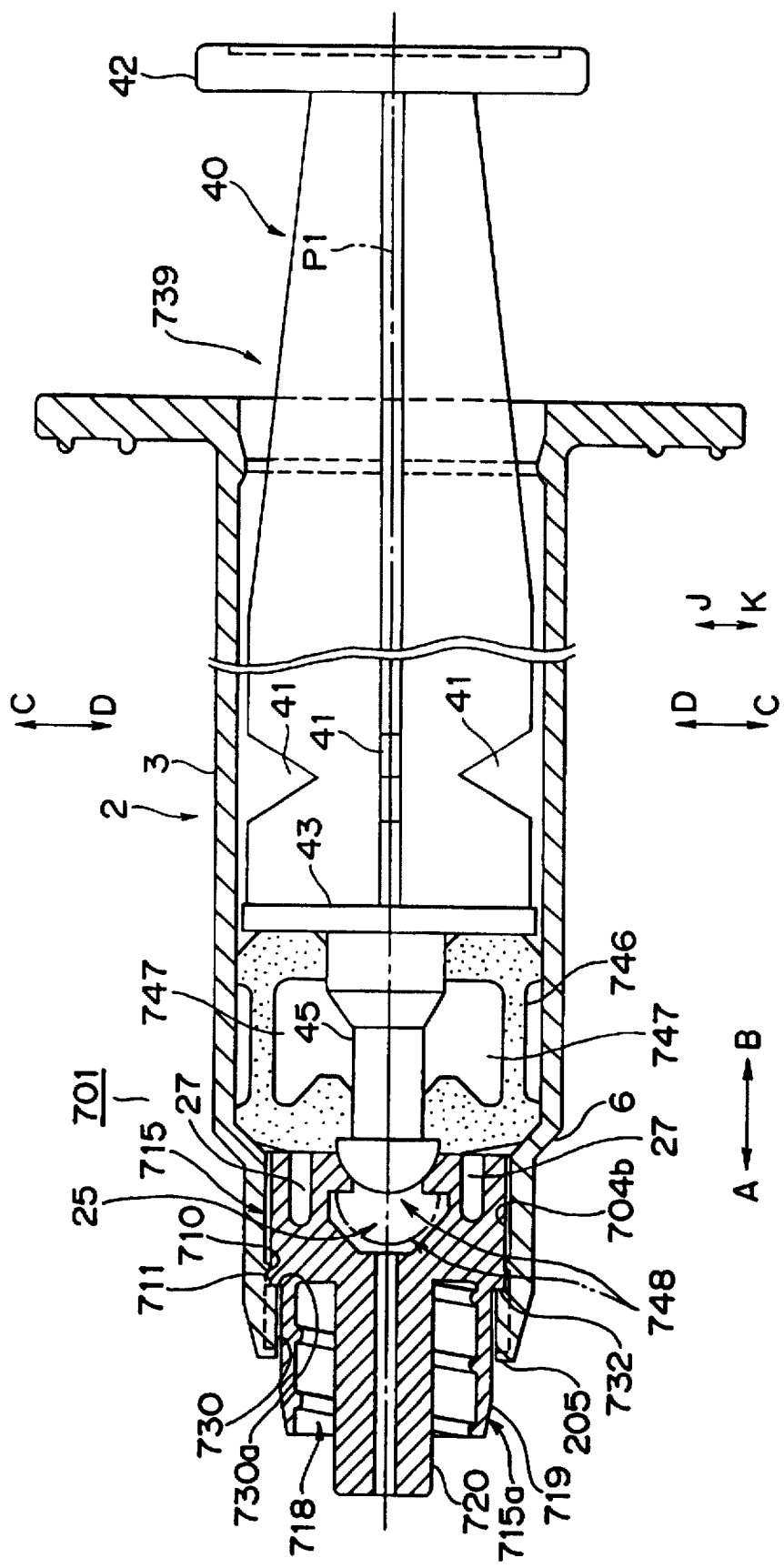
FIG. 14 is a typical sectional view showing an example of another syringe assembly according to the present invention.
Figure 15:
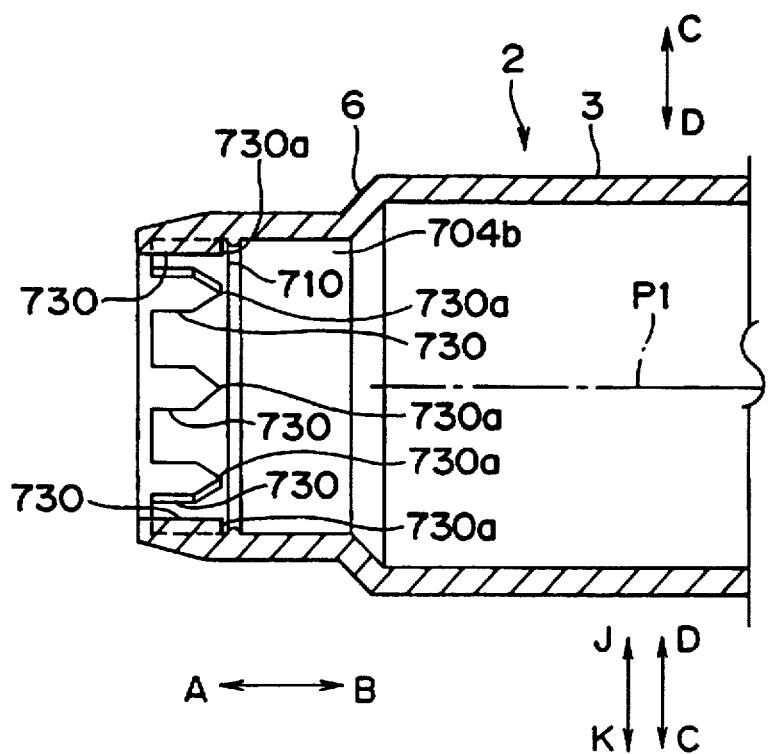
FIG. 15 is a sectional view showing only the syringe body side of the syringe assembly as shown in FIG. 14.
Figure 16:
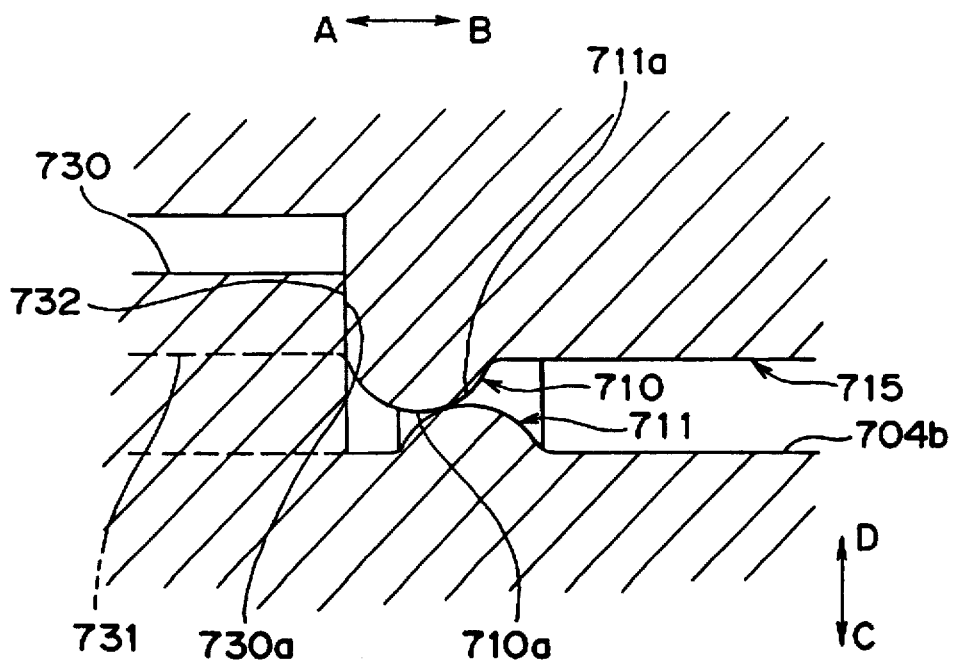
FIG. 16 is a sectional view showing near the projection for holding and the rib for holding in the syringe assembly as shown in FIG. 14.

Furthermore, the syringe assembly according to the present invention may be comprised as a syringe assembly 701 as shown in FIGS. 14 through 16. That is, the syringe assembly 701 is basically similar to the syringe assembly 201 in its structure. But, the positions of forming the projecting body for holding, such as the projection for holding 210, the projection for holding, such as the rib for holding 211, the rotation stop portion, such as the stopper portion 209, and the peripheral direction abutting portion, such as the peripheral direction abutting portion 221 are different. That is, in the syringe assembly 701, a projection for holding 710 which is a projecting body for holding is formed on the arrow B side rather than a stopper portion 730 which is a rotation stop portion, then a rib for holding 711 which is a projection for holding is formed on the arrow B side rather than a peripheral direction abutting portion 731 which is a peripheral direction abutting portion. Therefore, the top end of the arrow A side of the stopper portion 730 is communicated with the arrow B side of the end wall portion 205. Concerning the basic outside diameter of a main body 715a of a needle installation body 715, the side of the rib for holding 711 (that is, the arrow B side) is bigger than the side of the peripheral direction abutting portion 731 (that is, the arrow A side). Then, by the difference of these outside diameter, at the boundary position between the side of the rib for holding 711 and the side of the peripheral direction abutting portion 731, an abutting end face 732 facing the direction as shown by the arrow A is formed at the position excluding the peripheral direction abutting portion 731. In the state that the needle installation body 715 is installed in an installation space 704b, the projection for holding 710 and the rib for holding 711 contact with and abut on each other with a predetermined contact pressure, as shown in FIG. 14 and FIG. 16, and the abutting end face 732 and an end portion 730a of the arrow B side of the stopper portion 730 are contacted with and abutted on each other with a predetermined contact pressure, thereby the needle installation body 715 is engaged being compressed in the direction as shown by the arrows A and B between the projection for holding 710 and the stopper portion 730. Similar to the projection for holding 10 of the syringe assembly 1, the projection for holdings the section in the arc shape having a top end 710a where the distance from the axis center P1 is minimum, similar to the top end 10a. Similar to the rib for holding 11 of the syringe assembly 1, the rib for holding 711 is the section in the arc shape having a top end 711a where the distance from the axis center P1 is maximum, similar to the top end 11a. A cylindrical portion 719 is provided on the arrow A side of the needle installation body 715. A screw hole for hub 718 is provided with the cylindrical portion 719. Furthermore, inside of the cylindrical portion 719, a taper for hub 720 is provided projecting in the direction as shown by the arrow A.

The assembly of the syringe assembly 701 comprised heretofore is executed by installing the needle installation body 715 in the installation space 704b through the inside space side of the syringe body, similar to the assembly of the syringe assembly 201. The use of the syringe assembly 701 and its disposal after use is almost similar to the syringe assembly 201.

As shown in FIG. 14, a clearance portion 747 (which is a hollow space in FIG. 14, but a high flexibility member, such as sponge, may be filled as another embodiment) may be provided in a packing 746 of a piston 739. At the time of engagement between the piston 739 and the needle installation body 715, the packing 746 of the piston 739 is strongly pressed against the needle installation body 715 so as to compress and deform, then a hub engagement portion 748 of the piston 739 side is pushed out on the needle installation body 715 side. On this occasion, by providing the clearance portion 747 in the packing 746, the compression and deformation of the packing 746 is easy, then pushing out of the hub engagement portion 748 to the needle installation body 715 side is smooth and the engagement between the piston 739 and the needle installation body 715 is smooth.

Figure 17:
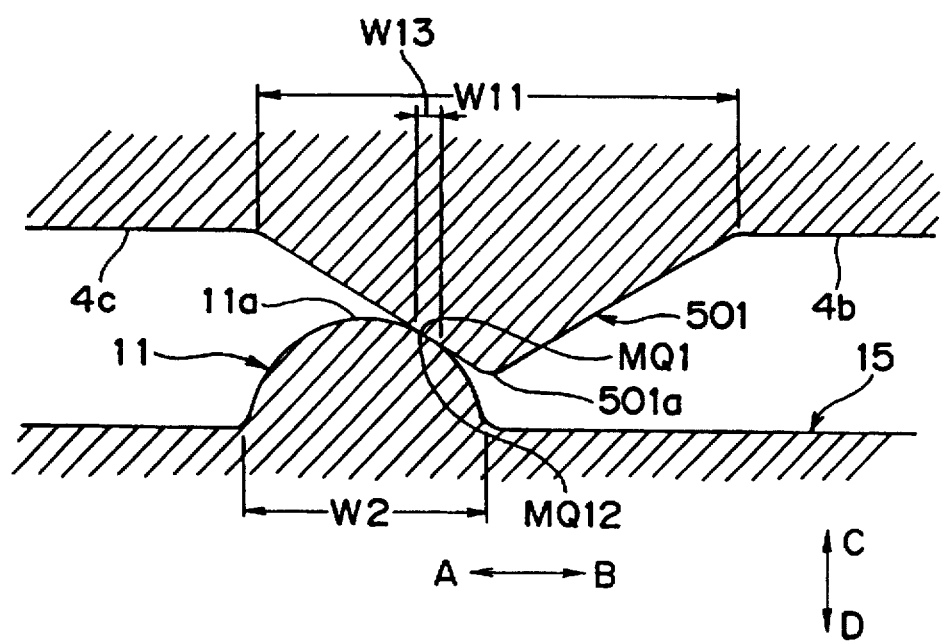
FIG. 17 is a sectional view showing near the projection for holding, formed in the shape different from the projection for holding as shown in FIG. 3, and the rib for holding.
Figure 18:
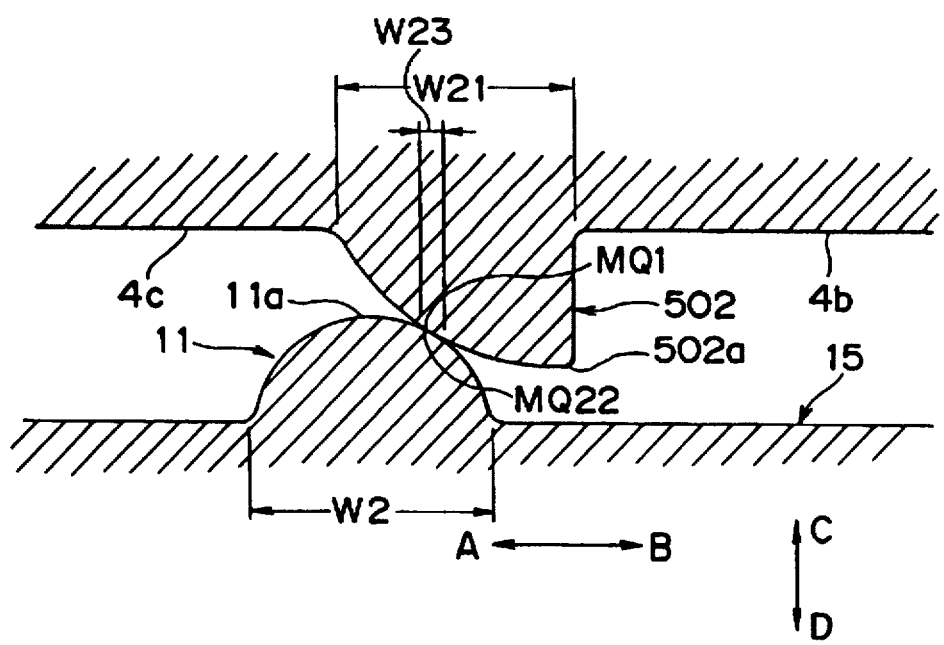
FIG. 18 is a sectional view showing near the projection for holding, formed in the shape different from the projection for holding as shown in FIG. 3, and the rib for holding.
Figure 19:
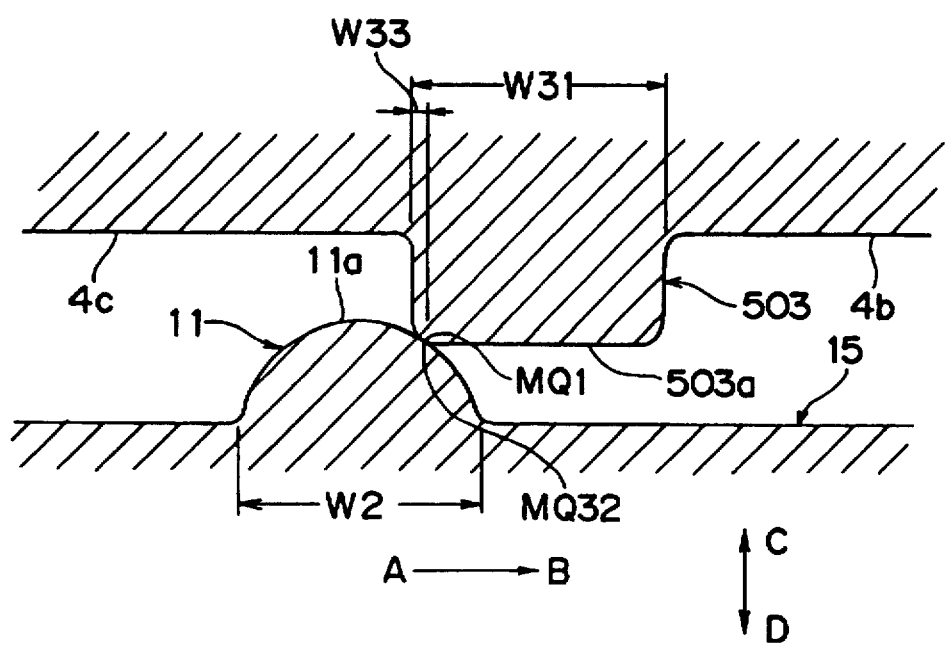
FIG. 19 is a sectional view showing near the projection for holding, formed in the shape different from the projection for holding as shown in FIG. 3, and the rib for holding.
Figure 20:
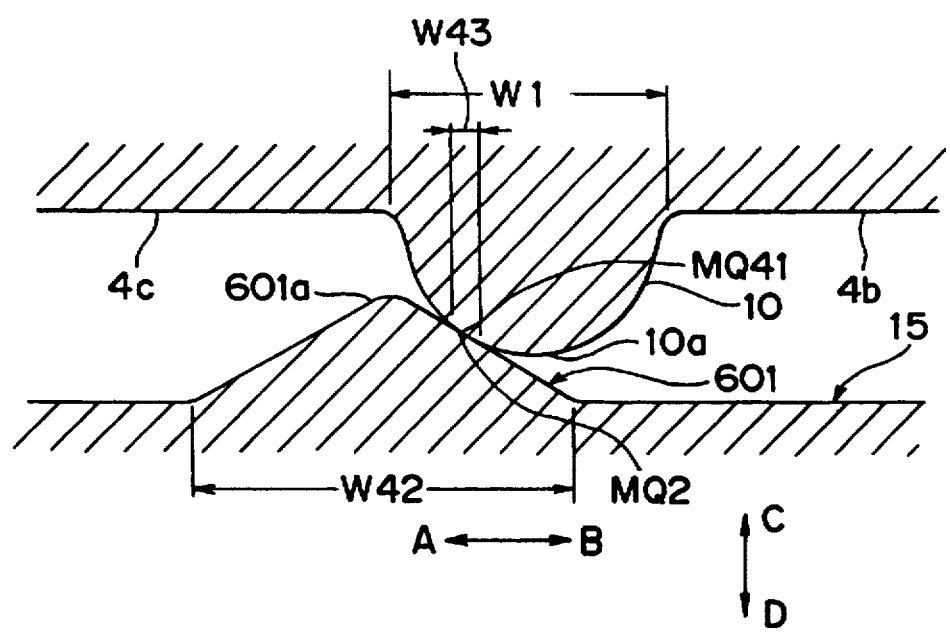
FIG. 20 is a sectional view showing near the rib for holding, formed in the shape different from the rib for holding as shown in FIG. 3, and the projection for holding.
Figure 21:
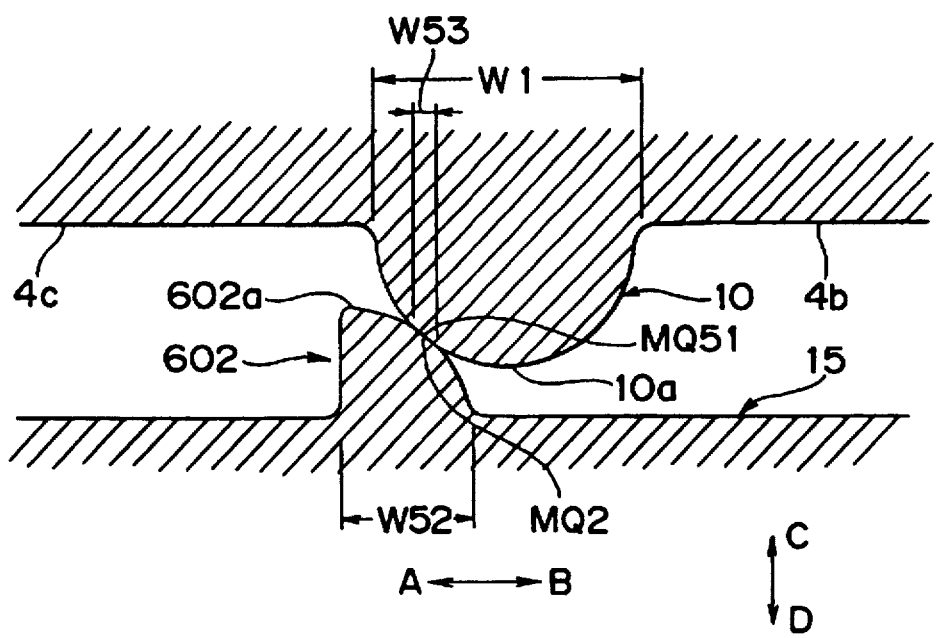
FIG. 21 is a sectional view showing near the rib for holding, formed in the shape different from the rib for holding as shown in FIG. 3, and the projection for holding.
Figure 22:
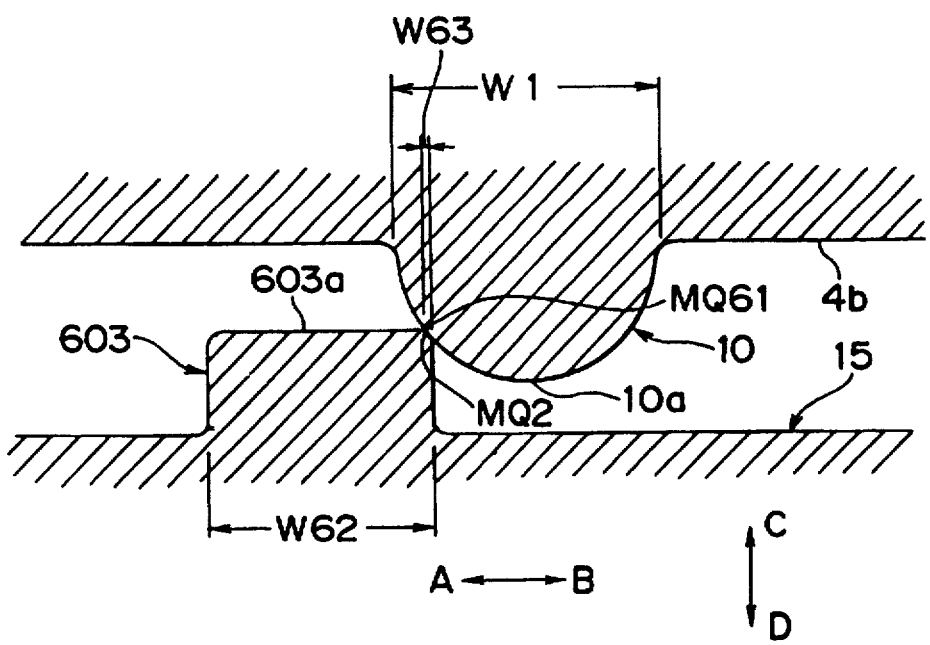
FIG. 22 is a sectional view showing near the rib for holding, formed in the shape different from the rib for holding as shown in FIG. 3, and the projection for holding.

In the bofore-mentioned respective embodiments, in the projecting body for holding, such as the projections for holding 10, 210, 410, 710, and the projection for holding, such as the ribs for holding 11, 211, 411, 711, the section shape including the axis center P1 is all arc shape, as shown in FIG. 3 shown with the projection for holding 10 and the rib for holding 11 as its example. But, the shape of the projecting body for holding and the projection for holding may be another one if the projection for holding can receive a compression force in the component of the direction as shown by the arrow A from the projecting body for holding at the time of installation. For instance, as shown in FIG. 17, the projection for holding 501 which is a projecting body for holding may be formed so as to make the section shape including the axis center P1 triangulate (in this case, the projection for holding 501 has the top end 501a which is an apex of a triangle in the section as the position where the distance from the axis center P1 is minimum. And, the positions MQ1, MQ12 which are the seal portions where the rib for holding 11 and the projection for holding 501 are abutting on each other, are formed with a width W13 which is smaller than any of a width W11 of the projection for holding 501 and the width W2 of the rib for holding 11 in the direction as shown by the arrows A and B). Alternatively, as shown in FIG. 18, a projection for holding 502 which is the projecting body for holding may be formed in such a manner that the section shape including the axis center P1 is one dividing the projection for holding 10 into two, lacking the arrow B side of the projection for holding 10 in the arc shape (in this case, the projection for holding 502 has a top end 502a which is the division position dividing the arc into a half as the position where the distance from the axis center P1 is minimum. And, the positions MQ1, MQ22 which are the seal portions of the rib for holding 11 and the projection for holding 502 are formed with a width W23 which is smaller than any of a width W21 of the projection for holding 502 and the width W2 of the rib for holding 11 in the direction as shown by the arrows A and B) (In this case, the liquid flow thin tube holding member, such as the needle installation body 15, is hard to be installed from the rear end side of the syringe body). Alternatively, as shown in FIG. 19, a projection for holding 503 which is a projecting body for holding may be formed so as to make the section shape including the axis center P1 square (in this case, the projection for holding 503 has a top end 503a which is one side parallel to the axis center P1 of the fours sides of the square in the section as a position where the distance from the axis center P1 is minimum. Besides, the positions MQ1, MQ32 which are seal portions of the rib for holding 11 and the projection for holding 503 is formed with a width W33 smaller than any of a width W31 of the projection for holding 503 and the width W2 of the rib for holding 11 in the direction as shown by the arrows A and B). And, as shown in FIG. 20, a rib for holding 601 which is a projection for holding may be formed so as to make the sectional form including the axis center P1 triangle (in this case, the rib for holding 601 has a top end 601a which is an apex of the triangle in the section as the position where the distance from the axis center P1 is maximum. And, the positions MQ41, MQ2 which are the seal portions of the rib for holding 601 and the projection for holding 10 are formed with a width W43 smaller than any of the width W1 of the projection for holding 10 and a width W42 of the rib for holding 601 in the direction as shown by the arrows A and B). Alternatively, as shown in FIG. 21, a rib for holding 602 which is a projection for holding may be formed so as to make the sectional form including the axis center P1 one dividing the rib for holding 11 into two, lacking the arrow A side of the rib for holding 11 of the arc shape (in this case, the rib for holding 602 has a top end 602a which is a division position dividing the arc into two as the position where the distance from the axis center P1 is maximum. And, the positions MQ51, MQ2 which are the seal portions of the rib for holding 602 and the projection for holding 10 are formed with a width W53 smaller than any of the width W1 of the projection for holding 10 and a width W52 of the rib for holding 602 in the direction as shown by the arrows A and B) (on this occasion, the liquid flow thin tube holding member, such as the needle installation body 15, is hard to be installed from the rear end side of the syringe body). Alternatively, as shown in FIG. 22, a rib for holding 603 which is a projection for holding may be formed so as to make the sectional shape including the axis center P1 square (in this case, the rib for holding 603 has a top end 603a which is the side parallel to the axis center P1 of the four sides of the square in the section as the position where the distance from the axis center P1 is maximum. And, the positions MQ61, MQ2 which are the seal portions of the rib for holding 603 and the projection for holding 10 are formed with a width W63 smaller than any of the width W1 of the projection for holding 10 and a width W62 of the rib for holding 603 in the directions as shown by the arrows A and B).

In the embodiments mentioned hereinbefore, the syringe body 2 and the needle installation bodies 15, 215, 415, 715 which are liquid flow thin tube holding members are made of resin. For instance, the materials, such as polyurethane, polyvinyl chloride, polypropylene, polyethylene can be used for the main bodies, 15a, 215a, 415a, 715a which are member main bodies of the liquid flow thin tube holding member.

As another embodiment, it is also effective to form the member main body of the liquid flow thin tube holding member with the material softer than the syringe body (including the portions of the projections for holding 10, 210, 410, 501, 502, 503, 710 which are projecting bodies for holding). In the concrete, the hardness of the syringe body side is made the boundary of 70–125 in Rockwell Hardness (R scale) and the hardness of the member main body is made the boundary of 40115 in Rockwell Hardness (R scale), and the hardness of the syringe body side is made harder than one of the member main body (that is, Rockwell Hardness of the syringe body side is made bigger than one of the member main body). As an example of this, the member main body is made with synthetic rubber or the like, thereby when the ribs for holding 11, 211, 411, 601, 602, 603, 711 which are the projections for holding of the member main body and the projections for holding 10, 210, 410, 501, 502, 503, 710 which are projecting bodies for holding of the syringe body are abutted on and engaged with each other, the projection for holding appropriately elastically deforms by its flexibility, then is easy to closely contact with the projecting body for-holding. As the result, the sealing between the projection for holding and the projecting body for holding is made more certain, and the member main body is more certain fixed with respect to the syringe body.

Furthermore, as another embodiment, it is also effective to form the main bodies 15a, 215a, 415a, 715a, which are member main bodies, of the needle installation bodies 15, 215, 415, 715, which are liquid flow thin tube holding members, by a known method of forming with two different materials. In the concrete, the ribs for holding 11, 211, 411, 601, 602, 603, 711 which are the projections for holding of the member main body are formed with the material softer than other portions of the member main body, and softer than the projections for holding 10, 210, 410, 501, 502, 503, 710 which are the projecting bodies for holding of the syringe body. In the concrete, the hardness of the syringe body side is made the boundary of 70–125 in Rockwell Hardness (R scale), the hardness of the projection for holding is made the boundary of 40–115 in Rockwell Hardness (R scale), and the hardness of the projecting body of holding of the syringe body side is made harder than one of the projection for holding liquid (that is, Rockwell Hardness of the projecting body for holding of the syringe body side is made harder than one of the projection for holding. On this occasion, it is available that the hardness of the portions excluding the projection for holding of the member main body is similar to one of the projecting body for holding of the syringe body side). As an example, the projection for holding of the member main body is made of polycarbonate, and other portions are made of polyurethane, thereby when the projection for holding is abutted on and engaged with the projecting body for holding of the syringe body 2 side, the projection for holding elastically deforms by its flexibility so as to easily closely contact with the projecting body for holding. In the result, the sealing between the projection for holding and the projecting body for holding is made more certain and fixing of the liquid flow thin tube holding member with respect to the syringe body is made more certain.

The present invention has been explained on the basis of the embodiments presented herein. However, the embodiments which are described in the present specification are illustrative and not limiting. The scope of the invention is designated by the accompanying claims and is not restricted by the descriptions of the specific embodiments. Accordingly, all the transformations and changes belonging to the claims are included in the scope of the present invention.

I claim:
1. A syringe assembly, comprising:

a syringe body;

a piston installed in said syringe body slidable in an axial center direction of said syringe body;

a holding member installation space cylindrically formed at a top end of said syringe body;

a penetrating hole formed at a top end of said holding member installation space communicating said holding member installation space and an outside of said syringe body with each other;

a liquid flow thin tube holding member capable of connecting with a liquid flow thin tube member attachably and detachably connected with said holding member installation space, said syringe assembly further comprising:

a projecting body for holding having a first width in said axial center direction of said syringe body, annularly formed along a plane perpendicular to said axial center direction of said syringe body at an inner peripheral portion of said holding member installation space;

a stopper for holding formed in said holding member installation space on said top end side of said syringe body rather than said projecting body for holding;

said liquid flow thin tube holding member having a member main body which can be linearly inserted in said holding member installation space in said axial center direction of said syringe body and can be linearly pulled out of said holding member installation space into said syringe body in said axial center direction of said syringe body;

a stopper abutting portion formed at said member main body so as to abut the stopper abutting portion on said stopper for holding, facing said top end direction of said syringe body;

a projection for holding having a second width in said axial center direction of said member main body, annularly formed along a plane perpendicular to said axial center direction of said member main body at an outer peripheral portion of said member main body;

a member side engagement means provided with said member main body so as to be free to engage with said piston; and said syringe assembly wherein said projection for holding can be abutted on and engaged with said projecting body for holding and said stopper abutting portion can be abutted on and engaged with said stopper for holding respectively such that said member main body between said projection for holding and said stopper abutting portion receives a predetermined compressive stress from the projecting body for holding and said stopper for holding, and a seal portion formed between said projection for holding and said projecting body for holding is formed with a third width smaller than any of said second width of said projection for holding and said first width of said projecting body for holding in said axial center direction of said syringe body when said member main body is installed in said holding member installation space.

2. The syringe assembly as set forth in claim 1 wherein said projecting body for holding has a top end portion where a distance from said axial center of said syringe body is minimum, and a distance from said projecting body for holding to said axial center is made bigger for said top end direction of said syringe body on said top end side of said syringe body rather than said top end portion.

3. The syringe assembly as set forth in claim 2 wherein a distance from said projecting body for holding to said axial center is made bigger for an rear end direction of said syringe body on said rear end side of said syringe body rather than said top end portion.

4. The syringe assembly as set forth in claim 3 wherein a sectional shape by a plane including said axial center of said syringe body of said projecting body for holding is an arc shape.

5. The syringe assembly as set forth in claim 3 wherein a sectional shape by a plane including said axial center of said syringe body of said projecting body for holding is an triangle shape.

6. The syringe assembly as set forth in claim 1 wherein a sectional shape by a plane including said axial center of said syringe body of said projecting body for holding is a square shape.

7. The syringe assembly as set forth in claim 1 wherein said projection for holding has a projection top end portion where a distance from said axial center of said member main body is maximum, and a distance from said projection for holding to said axial center is made smaller for said rear end direction of said member main body on said rear end side of said member main body rather than said projection top end portion.

8. The syringe assembly as set forth in claim 7 wherein said distance from said projection for holding to said axial center is made smaller for said top end direction of said member main body on said top end side of said member main body rather than said projection top end portion.

9. The syringe assembly as set forth in claim 8 wherein a sectional shape by a plane including said axial center of said member main body of said projection for holding is an arc shape.

10. The syringe assembly as set forth in claim 8 wherein a sectional shape by a plane including said axial center of said member main body of said projection for holding is a triangle shape.

11. The syringe assembly as set forth in claim 1 wherein a sectional shape by a plane including said axial center of said member main body of said projection for holding is a square shape.

12. The syringe assembly as set forth in claim 1 wherein said projecting body for holding has a top end portion where a distance from said axial center of said syringe body is minimum, said projection for holding has a projection top end portion where a distance from said axial center of said member main body is maximum, and a seal portion which said projection for holding and said projecting body for holding abut on each other when said member main body is installed in said holding member installation space is between said top end portion and said projection top end portion in said axial center direction of said syringe body.

13. The syringe assembly as set forth in claim 1 wherein an outside diameter of portions excluding said projection for holding of said member main body is formed smaller than an inside diameter of a portion corresponding to said holding member installation space.

14. The syringe assembly as set forth in claim 1 wherein said liquid flow thin tube holding member can be inserted into said holding member installation space through said penetrating hole.

15. The syringe assembly as set forth in claim 14 wherein one or more than one slits are formed at a periphery of said penetrating hole.

16. The syringe assembly as set forth in claim 1 wherein a needle main body is directly connected with said member main body.

17. The syringe assembly as set forth in claim 16 wherein said member side engagement means and said needle main body are communicated with each other.

18. The syringe assembly as set forth in claim 1 wherein a taper for connecting liquid flow thin tube member is formed on said top end side of said member main body, projecting in a direction parallel to said axial center direction of said member main body.

19. The syringe assembly as set forth in claim 18 wherein a liquid flow thin tube member engagement portion is provided at a periphery of said taper for connecting liquid flow thin tube member of said member main body.

20. The syringe assembly as set forth in claim 19 wherein said liquid flow thin tube member engagement portion is a screw hole for installation cylindrically formed opening in a direction parallel to said axial center direction of said member main body.

21. The syringe assembly as set forth in claim 15 wherein said taper for connecting liquid flow thin tube member is formed on said top end side of said member main body, projecting in a direction parallel to said axial center direction of said member main body.

22. The syringe assembly as set forth in claim 18 wherein a rotation stop portion is formed at an inner peripheral portion of said holding member installation space, and a peripheral direction abutting portion is formed at an outer periphery portion of said member main body so as to prevent rotation of said member main body in a periphery direction with said axial center of said syringe body as its center by abutment in said periphery direction between said peripheral direction abutting portion and said rotation stop portion when said member main body is installed in said holding member installation space.

23. The syringe assembly as set forth in claim 19 wherein a rotation stop portion is formed at an inner peripheral portion of said holding member installation space, and a peripheral direction abutting portion is formed at an outer periphery portion of said member main body so as to prevent rotation of said member main body in a periphery direction with said axial center of said syringe body as its center by abutment in said periphery direction between said peripheral direction abutting portion and said rotation stop portion when said member main body is installed in said holding member installation space.

24. The syringe assembly as set forth in claim 1 wherein said member side engagement means has a groove formed in a direction perpendicular to said axial center direction of said member main body, penetrating said member main body.

25. The syringe assembly as set forth in claim 1 wherein a deformation accelerating groove is provided with said member main body on a side in a direction perpendicular to said axial center direction of said member main body of said member side engagement means.

26. The syringe assembly as set forth in claim 1 wherein a piston side engagement means capable of engaging with said member side engagement means of said liquid flow thin tube holding member is provided with said piston, facing said member side engagement means.

27. The syringe assembly as set forth in claim 1 wherein said piston is comprised such that a piston body can be bent and taken off between an operation portion and a medical liquid pressing portion.

28. The syringe assembly as set forth in claim 27 wherein a piston stopper is provided with said syringe body so as not to pull off said medical liquid pressing portion of said piston from said syringe body.

29. The syringe assembly as set forth in claim 27 wherein a notch for bending and taking off is formed at said piston body of said piston.

30. The syringe assembly as set forth in claim 29 wherein said notch is formed so as to position at an end portion of said syringe body when said piston is abutted on said piston stopper.

31. The syringe assembly as set forth in claim 1 wherein said member main body is formed with a material softer than one forming said projecting body for holding of said syringe body.

32. The syringe assembly as set forth in claim 1 wherein said member main body is formed by a method of forming with two different materials, having a first material and a second material softer than the first material and softer than the material forming said projecting body for holding of said syringe body, and said projection for holding is formed with the second material.

* * * * *